(12) United States Patent
Hanaoka et al.

(10) Patent No.: US 11,560,365 B2
(45) Date of Patent: Jan. 24, 2023

(54) NON-FLUORESCENT RHODAMINES

(71) Applicant: THE UNIVERSITY OF TOKYO, Tokyo (JP)

(72) Inventors: Kenjiro Hanaoka, Tokyo (JP); Yasuteru Urano, Tokyo (JP); Takayuki Ikeno, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 3 days.

(21) Appl. No.: 16/977,437

(22) PCT Filed: Mar. 4, 2019

(86) PCT No.: PCT/JP2019/008396
§ 371 (c)(1),
(2) Date: Nov. 25, 2020

(87) PCT Pub. No.: WO2019/168198
PCT Pub. Date: Sep. 6, 2019

(65) Prior Publication Data
US 2021/0087160 A1 Mar. 25, 2021

(30) Foreign Application Priority Data
Mar. 2, 2018 (JP) ............................. JP2018-038018

(51) Int. Cl.
C07D 311/82 (2006.01)
C09B 11/24 (2006.01)

(52) U.S. Cl.
CPC ............ *C07D 311/82* (2013.01); *C09B 11/24* (2013.01)

(58) Field of Classification Search
CPC ................................. C09B 11/24; C09B 11/28
See application file for complete search history.

(56) References Cited

U.S. PATENT DOCUMENTS

| 6,162,931 A | 12/2000 | Gee et al. | |
| 6,229,055 B1 | 5/2001 | Klaubert et al. | |
| 2003/0212126 A1* | 11/2003 | Habi | A61K 35/28 514/454 |
| 2006/0105335 A1 | 5/2006 | Daehne et al. | |

(Continued)

FOREIGN PATENT DOCUMENTS

| JP | 11-508277 A | 7/1999 |
| JP | 2003-267968 A | 9/2003 |

(Continued)

OTHER PUBLICATIONS

Luke Lavis (Annu. Rev. Biochem. 2017. 86:825-43).*

(Continued)

*Primary Examiner* — Valerie Rodriguez-Garcia
(74) *Attorney, Agent, or Firm* — Knobbe, Martens, Olson & Bear LLP

(57) ABSTRACT

A novel non-fluorescent rhodamine dye forms a twisted intramolecular charge transfer state. A substituent that causes steric hindrance is introduced at an ortho position of a dimethylamino group on the xanthene ring of tetramethylrhodamine, which is a general rhodamine that exhibits strong fluorescence, and a certain amount of twist is imparted in a ground state. As a result, the formation of the twisted intramolecular charge transfer state is promoted in the excited state and non-fluorescence is exhibited.

5 Claims, 18 Drawing Sheets

(56) References Cited

U.S. PATENT DOCUMENTS

| | | | |
|---|---|---|---|
| 2007/0098732 A1 | 5/2007 | Roy et al. | |
| 2009/0176869 A1 | 7/2009 | Habi et al. | |
| 2011/0021616 A1 | 1/2011 | Habi et al. | |
| 2011/0301573 A1 | 12/2011 | Habi et al. | |
| 2012/0135459 A1* | 5/2012 | Hell | C07D 311/82 435/7.1 |
| 2012/0136338 A1 | 5/2012 | Roy et al. | |
| 2014/0314720 A1 | 10/2014 | Habi et al. | |

FOREIGN PATENT DOCUMENTS

| | | |
|---|---|---|
| JP | 2004-518766 A | 6/2004 |
| JP | 2005-534931 A | 11/2005 |
| JP | 2007-513096 A | 5/2007 |
| WO | WO 2010/149190 A1 | 12/2010 |

OTHER PUBLICATIONS

Iwatate et al. (Chem. Eur. J. 2016, 22, 1696-1703).*
Butkevich et al., "Fluorescent Rhodamines and Fluorogenic Carbopyronines for Super-Resolution STED Microscopy in Living Cells", Angewandte Chemie. International Edition, vol. 55, No. 2016, vol. 10, pp. 3290-3294, (2016).
Ikeno et al., "Development of Fluorescent Probe Using Quenching Mechanism Based on Twisted Intramolecular Charge Transfer", Presentation Abstracts of the 138th Annual Conference (Kanazawa) of the Pharmaceutical Society of Japan, (2018).
Iwaki et al., "Analysis of N-Ph Rhodamine-Type Quenching Mechanism and its Application to Fluorescent Probe", JSMI Report, vol. 9, No. 1, pp. 40-42, (2015).
Johnson et al., "The Molecular Probes Handbook", pp. 78-81 (2010).
Ou et al., "pH-Sensitive Nanocarriers for Ganoderma Applanatum Polysaccharide Release Via Host-Guest Interactions", Journal of Materials Science, vol. 53, No. 11, pp. 7963-7975, (2018).
Wang et al., "Novel Reversible Mechanochromic Elastomer with High Sensitivity: Bond Scission and Bending-Induced Multicolor Switching", ACS Applied Materials & Interfaces, vol. 9, No. 13, pp. 11874-11881, (2017).
Yatzeck et al., "A Highly Sensitive Fluorogenic Probe for CytochromeP450 Activity in Live Cells", Bioorganic & Medicinal Chemistry Letters, vol. 18, No. 22, pp. 5864-5866, (2008).

\* cited by examiner

[Fig. 1]
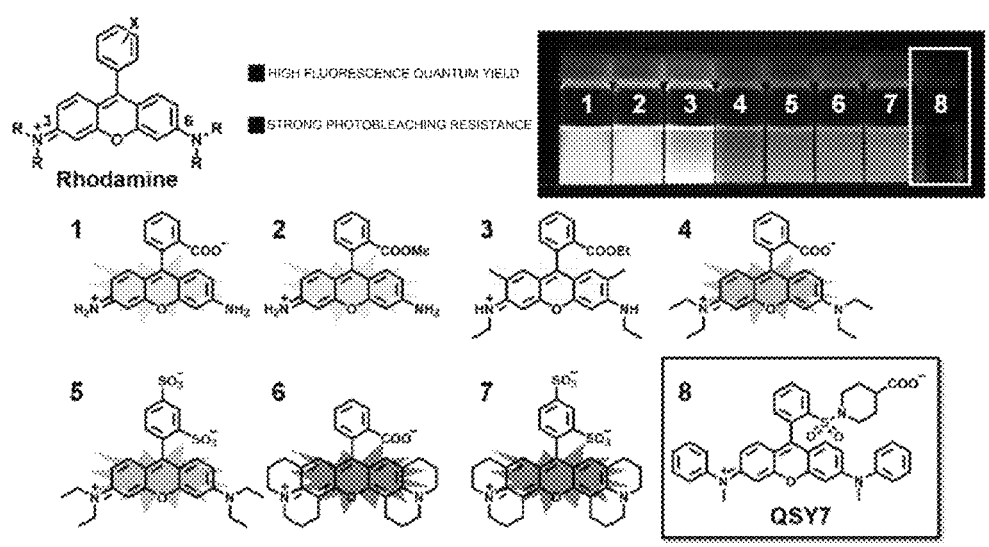

[Fig. 2]
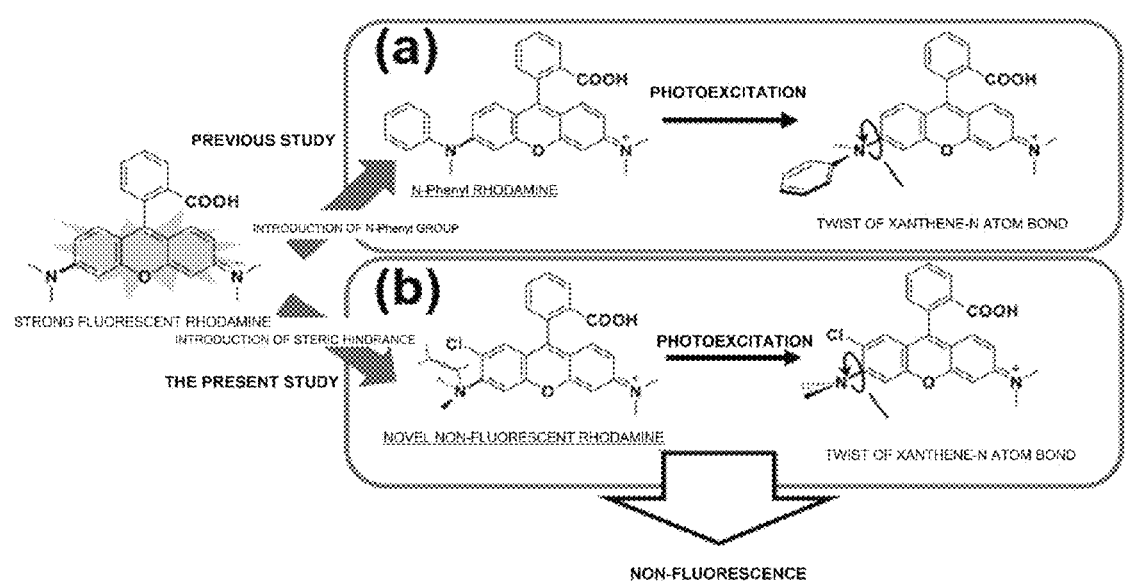

[Fig. 3]
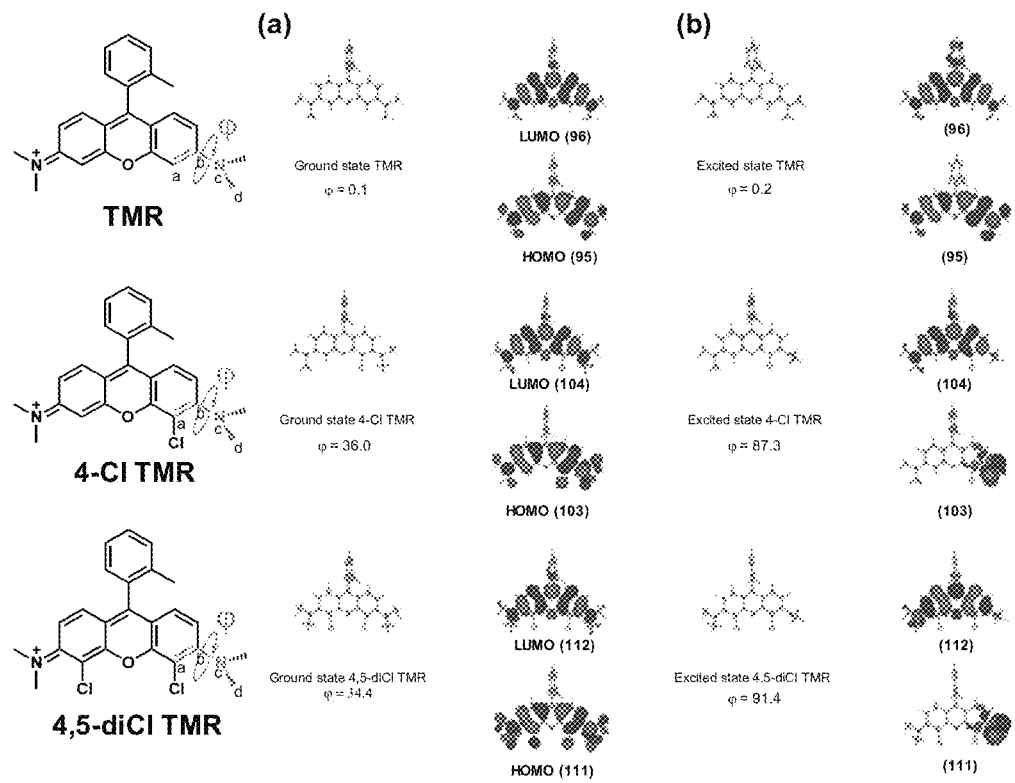
[Fig. 4]
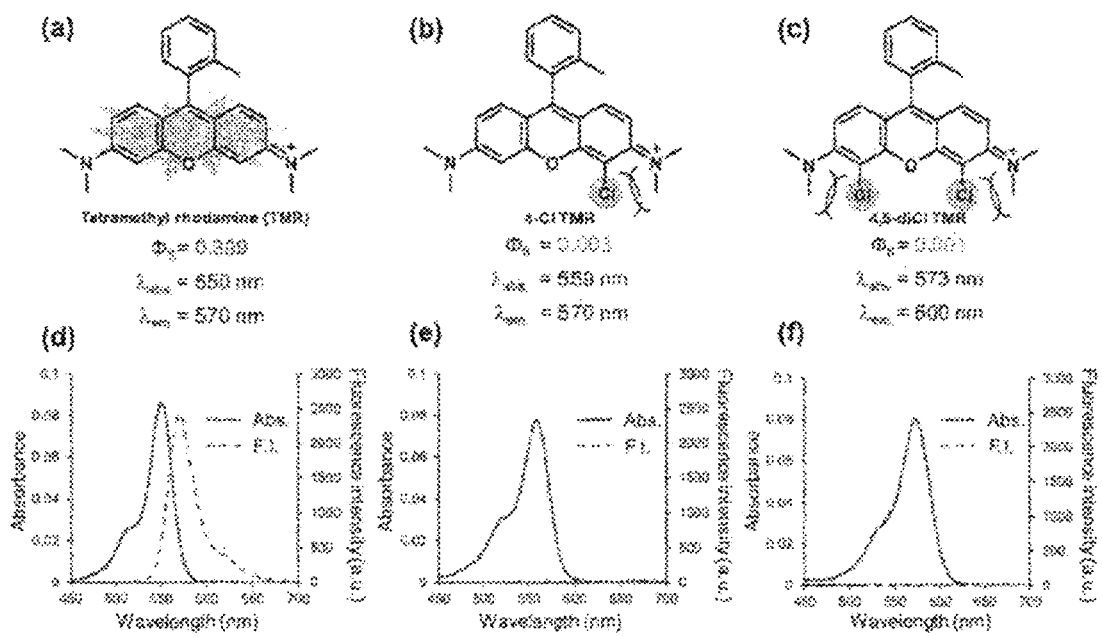

[Fig. 5]
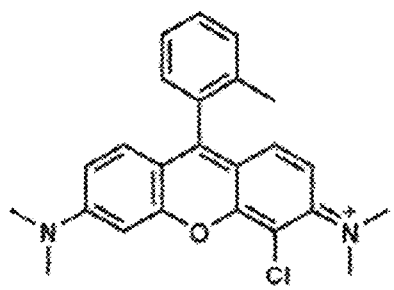
|  | η (cP) | Φ_fl |
|---|---|---|
| Glycerol | 1412 | 0.091 |
| Ethylene glycol | 19.9 | 0.010 |
| MeOH | 0.6 | 0.003 |
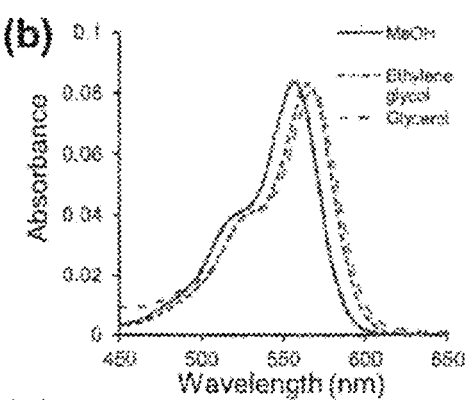
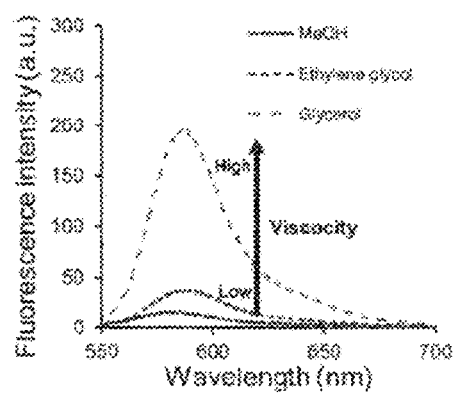

[Fig. 6]
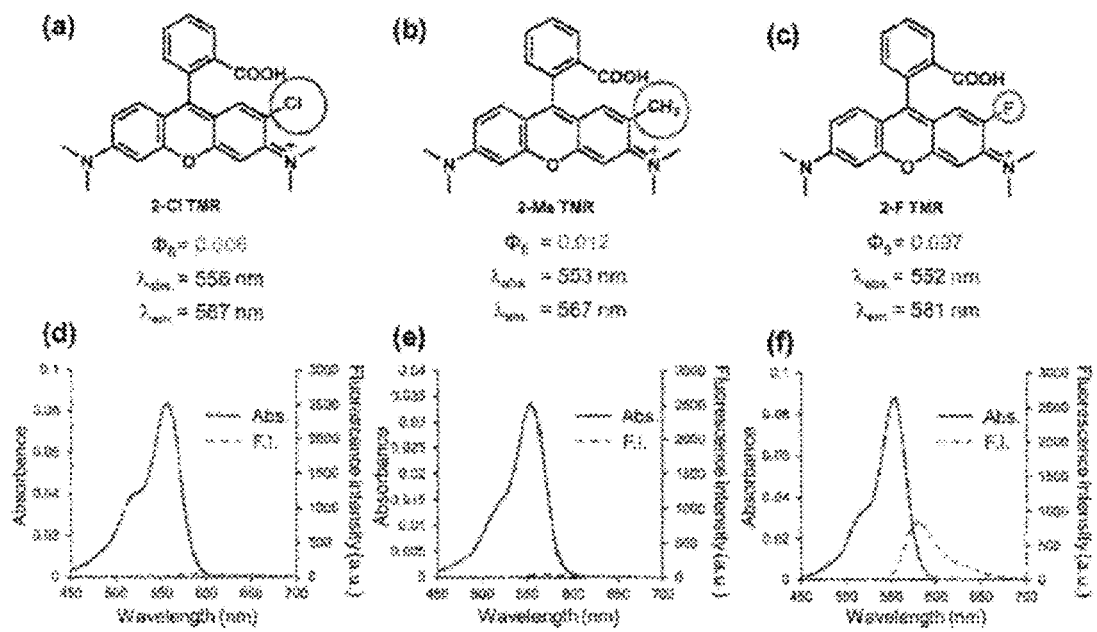
[Fig. 7]
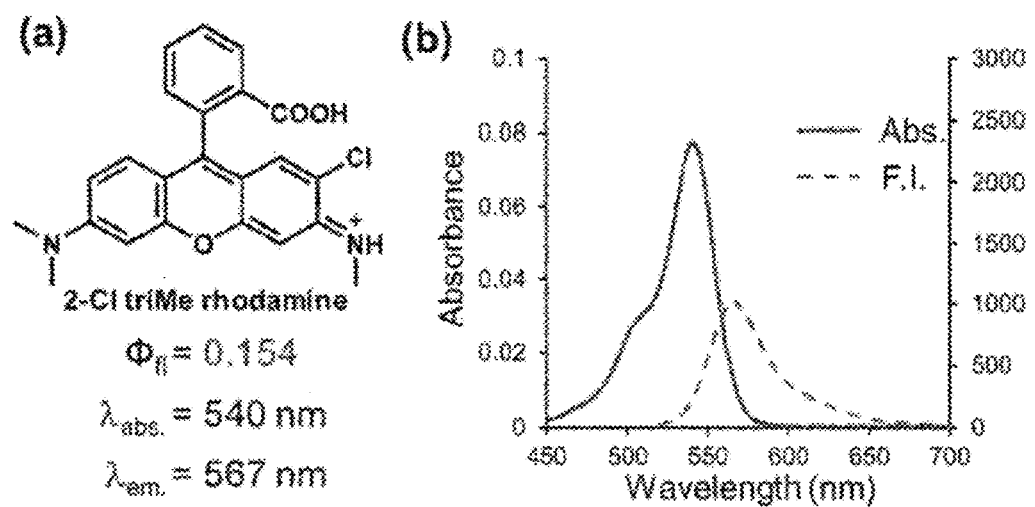

[Fig. 8]
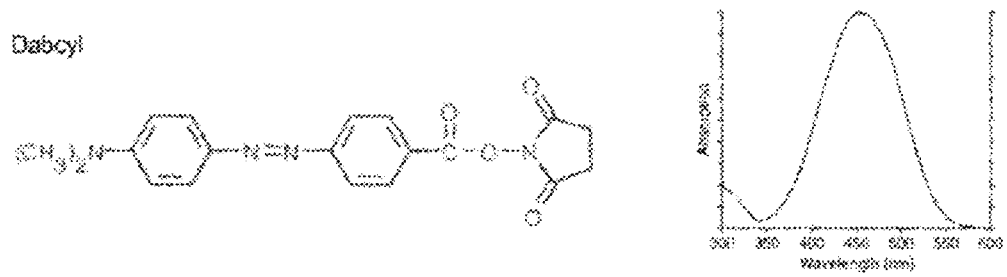
[Fig. 9]
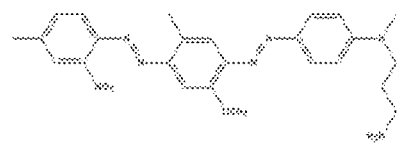
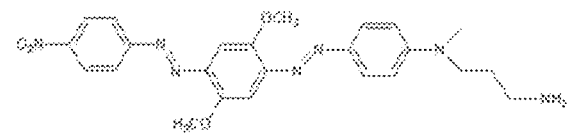
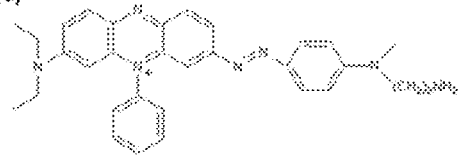
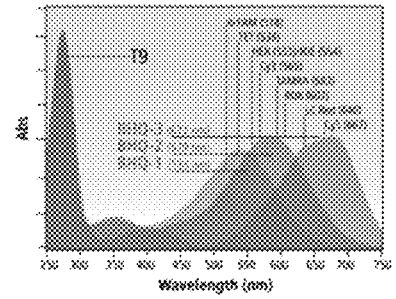
[Fig. 10]
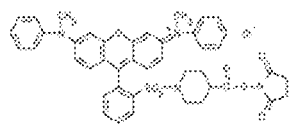
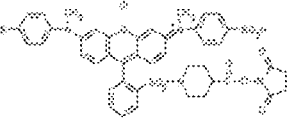

[Fig. 11]
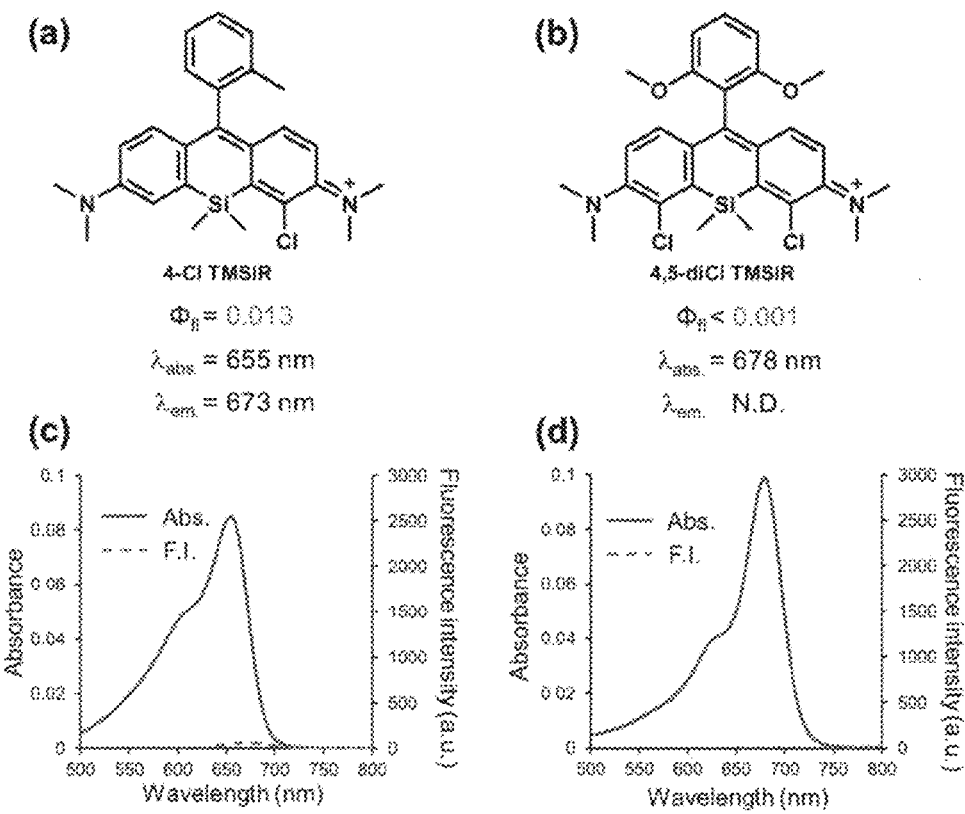
[Fig. 12]
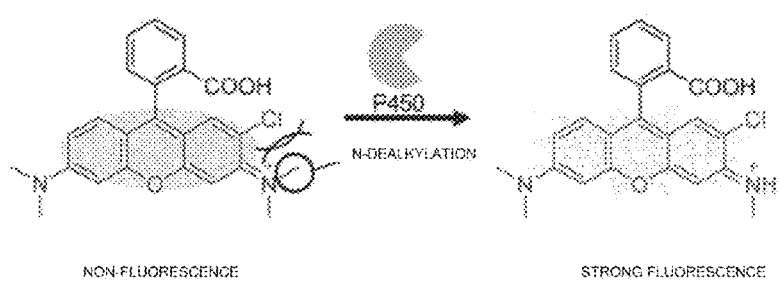

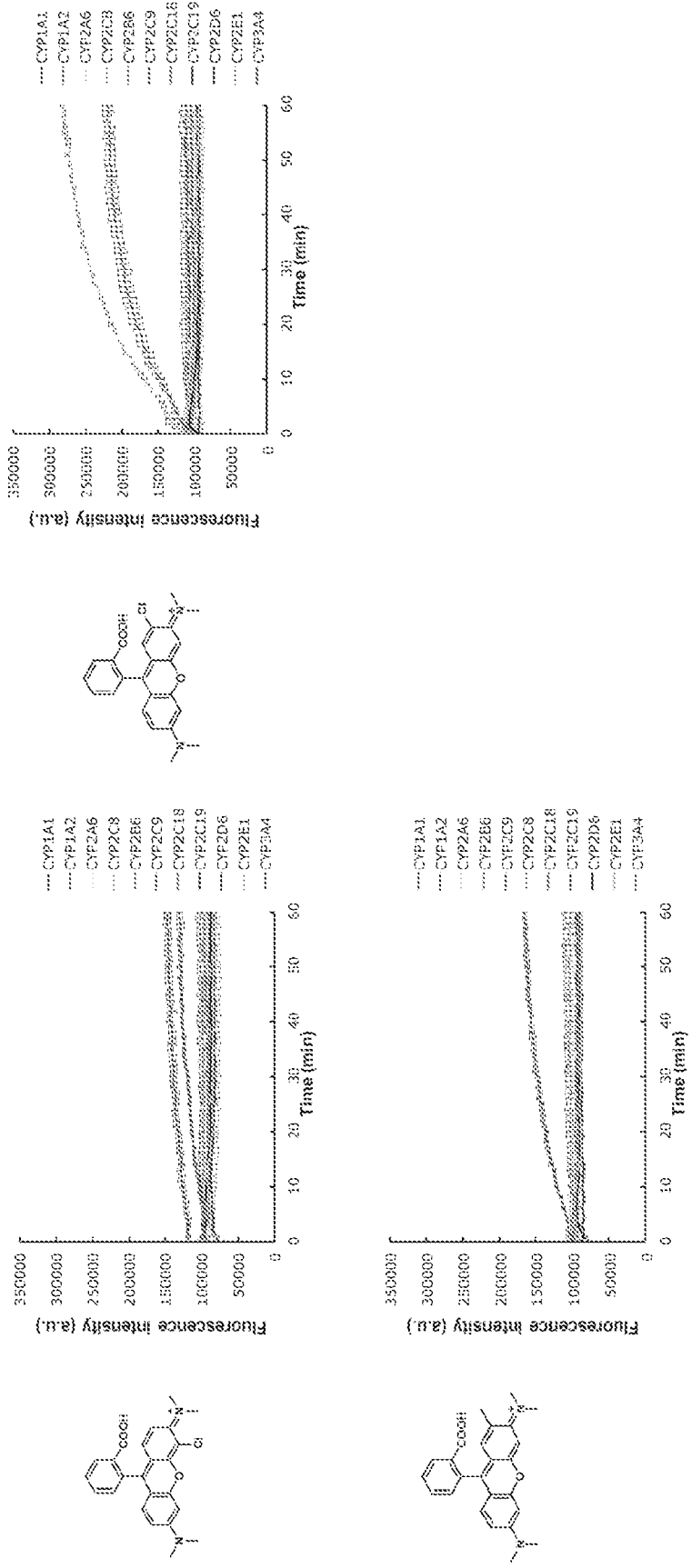
[Fig. 13]

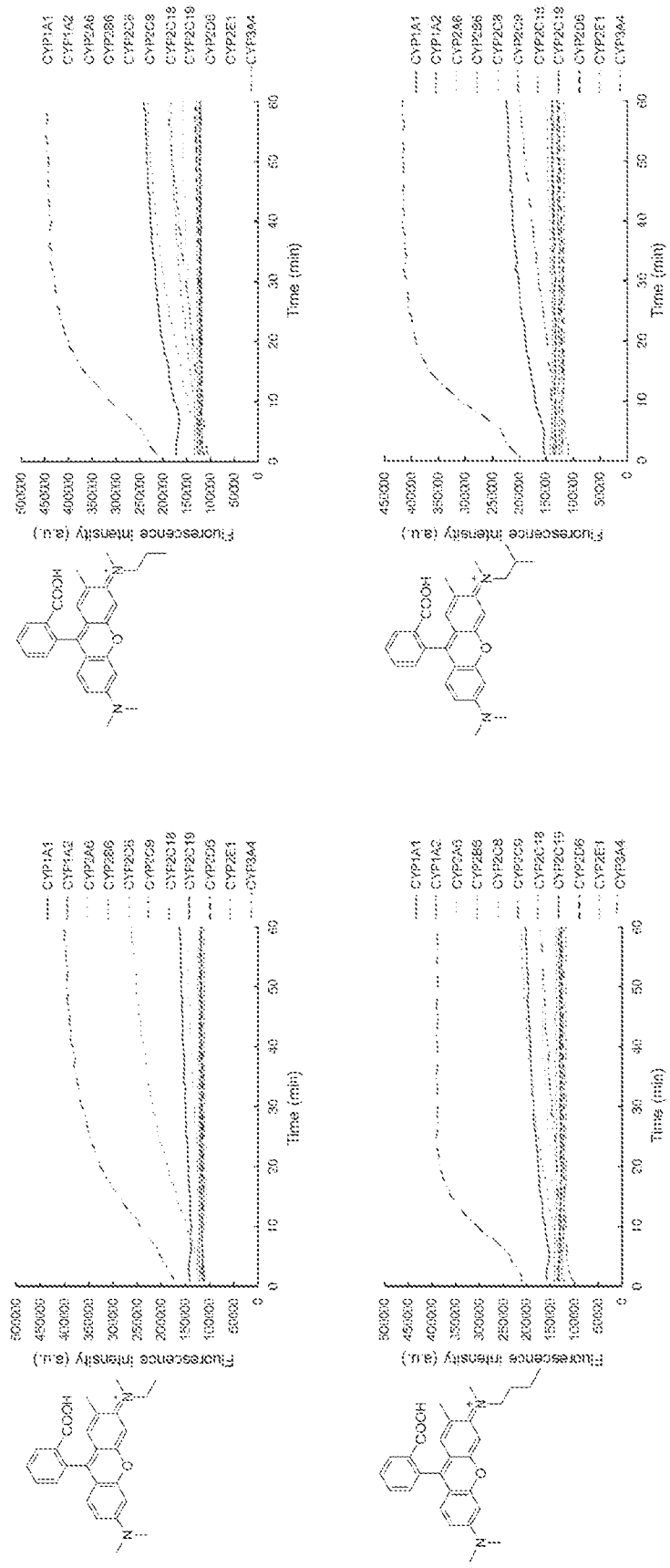
[Fig. 14]

[Fig. 16]
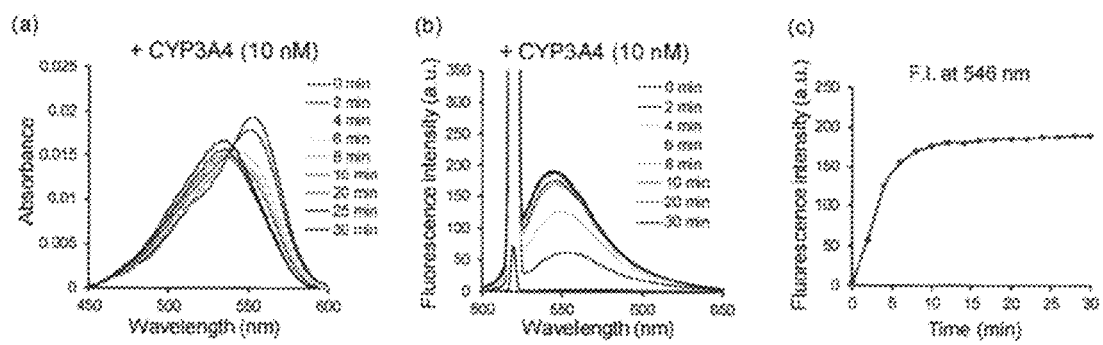
[Fig. 17]
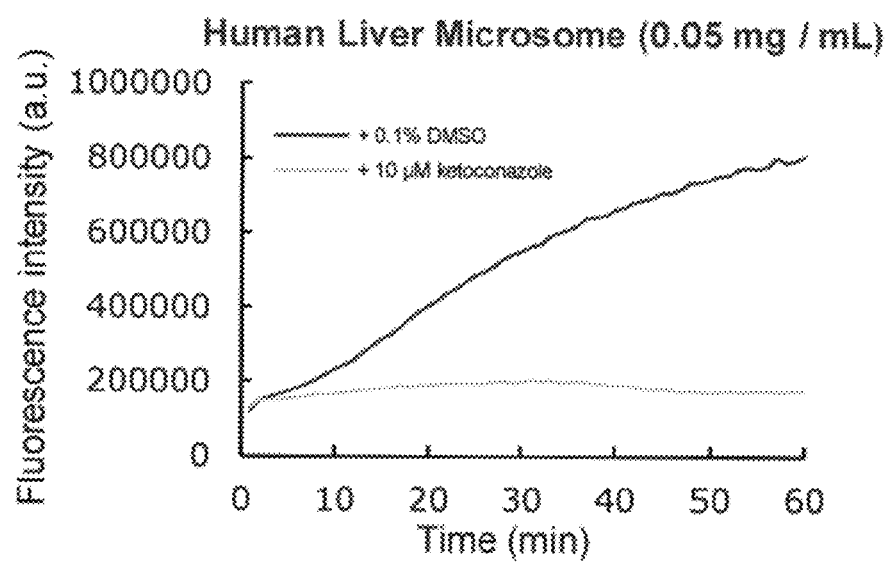

[Fig. 18]
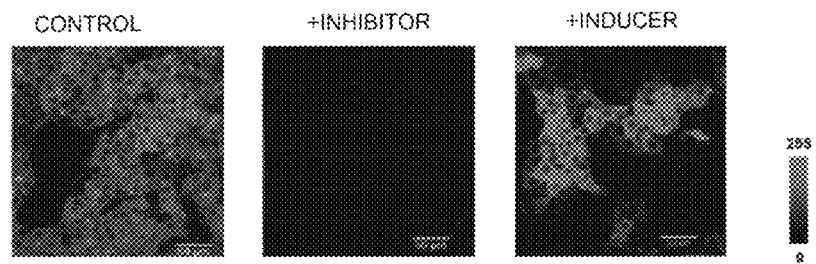
[Fig. 19]
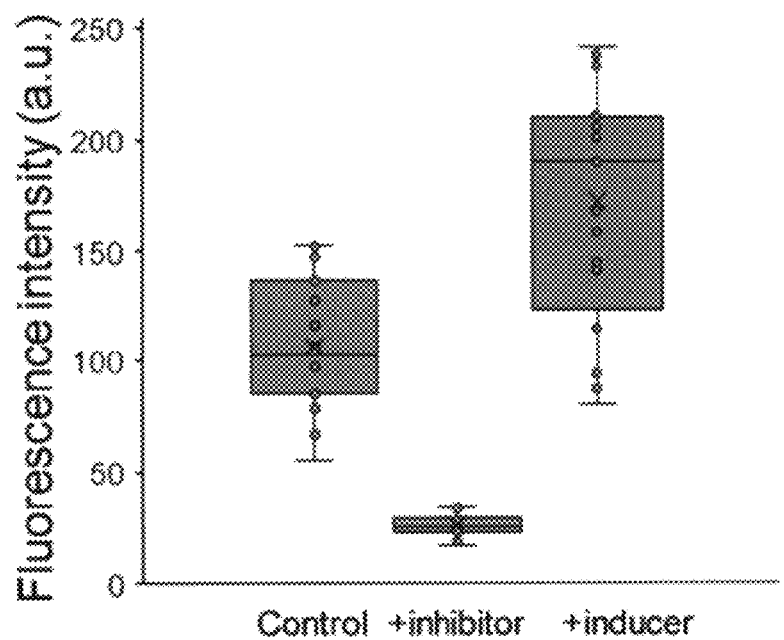

[Fig. 20]
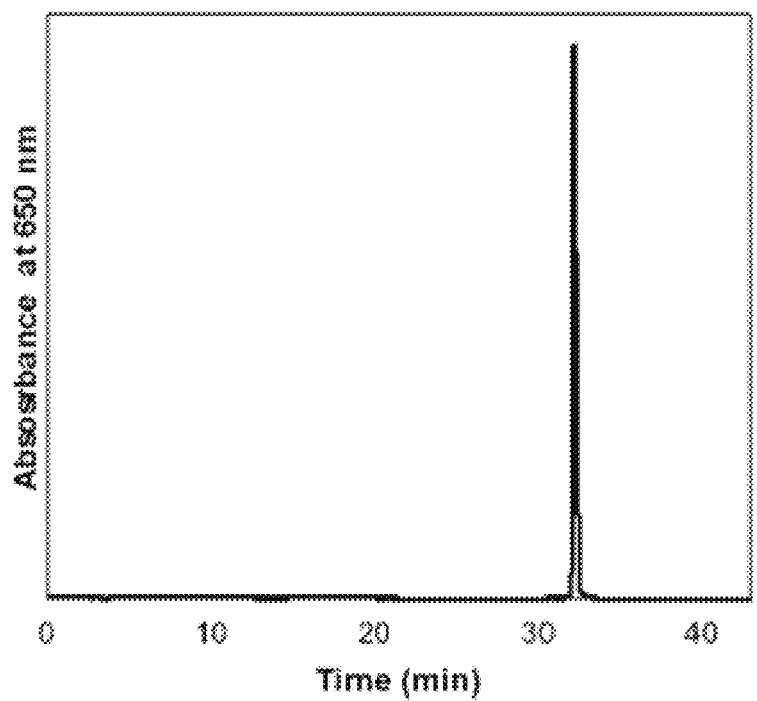

[Fig. 21]
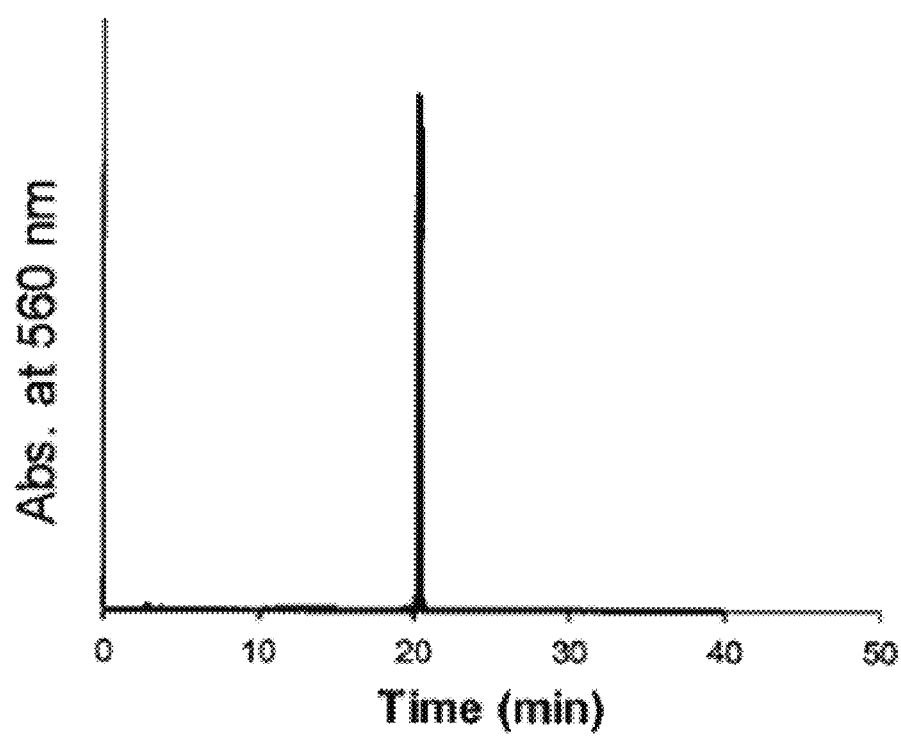

[Fig. 22]
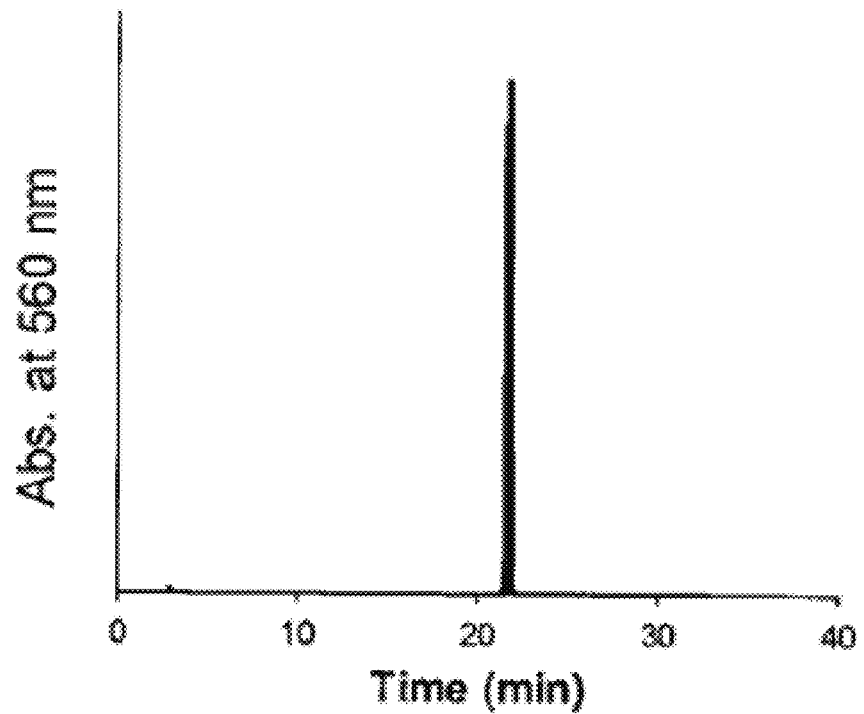

[Fig. 23]
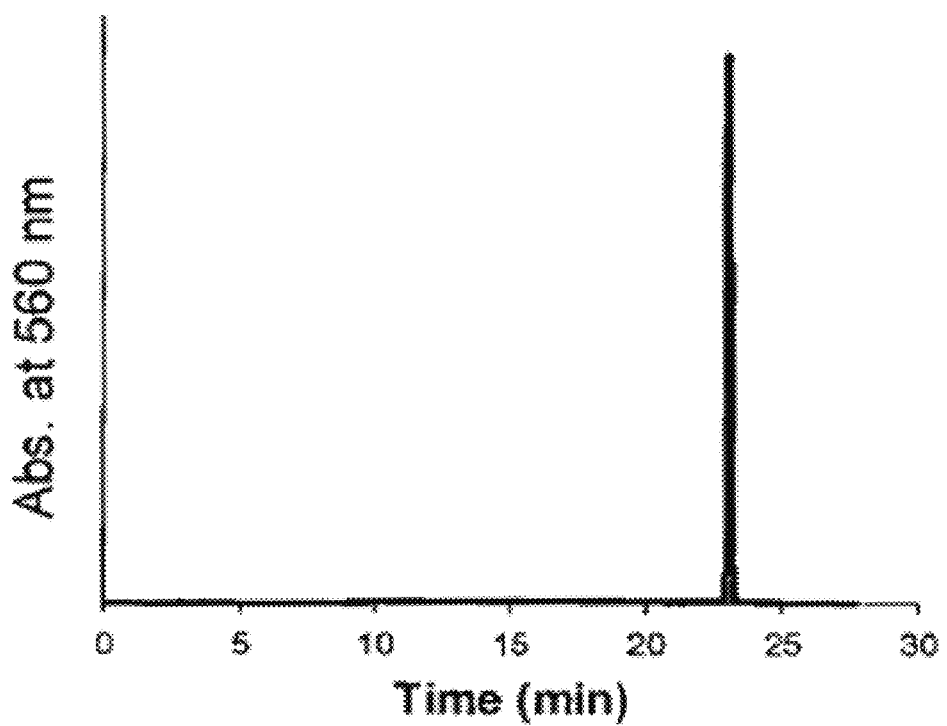

[Fig. 24]
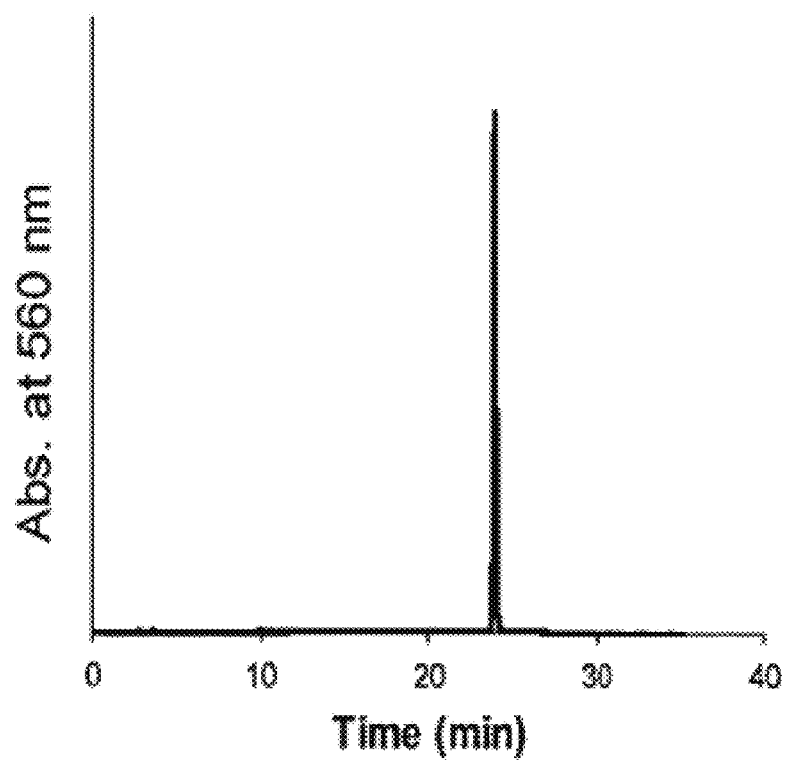

[Fig. 25]
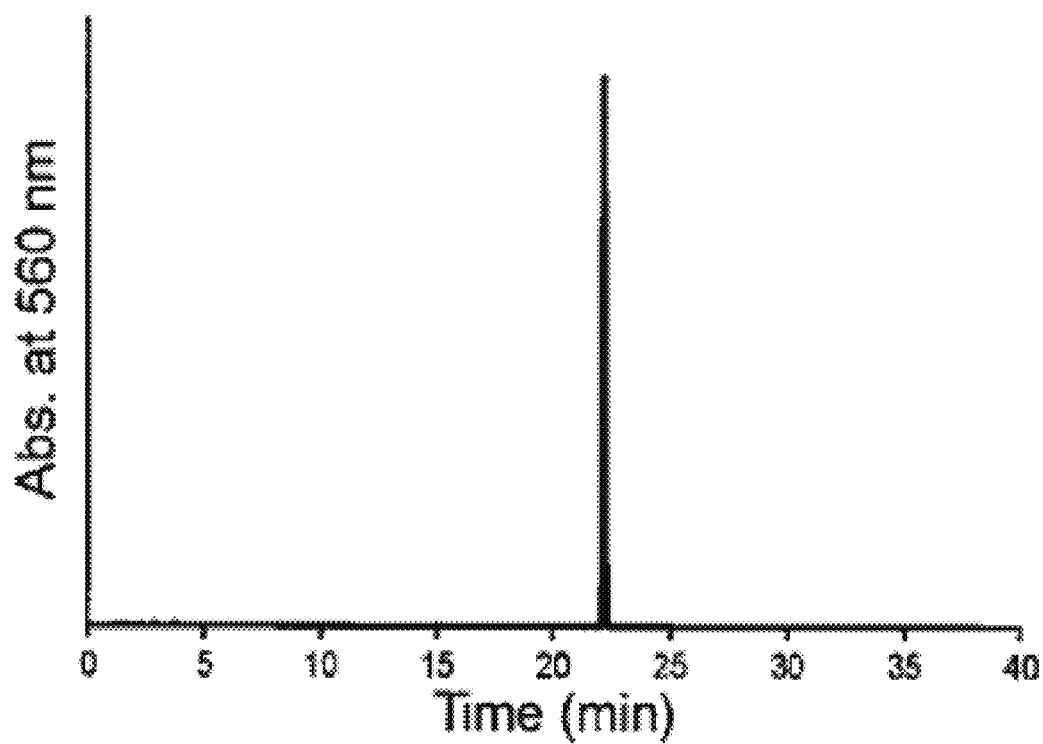

NON-FLUORESCENT RHODAMINES

PRIORITY AND CROSS REFERENCE TO RELATED APPLICATIONS

This application is the U.S. National Phase Application under 35 U.S.C. § 371 of International Application No. PCT/JP2019/008396, filed Mar. 4, 2019, designating the U.S. and published as WO 2019/168198 A1 on Sep. 6, 2019, which claims the benefit of Japanese Application No. JP 2018-038018, filed Mar. 2, 2018. Any and all applications for which a foreign or a domestic priority is claimed is/are identified in the Application Data Sheet filed herewith and is/are hereby incorporated by reference in their entirety.

TECHNICAL FIELD

The present invention relates to novel non-fluorescent rhodamines, and more particularly to novel non-fluorescent rhodamines based on a TICT mechanism.

BACKGROUND ART

Rhodamines are a general term for dyes in which nitrogen atom is bonded to the 3- and 6-positions of the xanthene ring, and have been widely used in fluorescence imaging as dyes that have water solubility together with high fluorescence quantum yield and strong photobleaching resistance (FIG. 1).

On the other hand, some rhodamines exhibit non-fluorescence due to some quenching mechanism. Such "non-fluorescent rhodamines" are not only used as quenchers that serve as FRET acceptors to quench the fluorescence of a donor molecule, but also elucidate the mechanism of their non-fluorescence and suitably designs molecules to release the non-fluorescence by using specific life phenomena as triggers, so that a fluorescent probe based on a new fluorescence control principle can be developed.

QSYs that are typical non-fluorescent rhodamines are dyes in which an aromatic ring is bonded to N atom on the xanthene ring of rhodamine (hereinafter also referred to as "N-phenylrhodamines"). Although the reason why these N-phenylrhodamines become non-fluorescent has not been analyzed in detail so far, the present inventors' previous studies have suggested that this quenching occurs due to production of a TICT (Twisted intramolecular charge transfer) state in an excited state (see FIG. 2(a)). TICT is a phenomenon in which a charge imbalance (ICT) in the molecule occurs in the excited state, and, at the same time, a twist of the molecular structure occurs.

CITATION LIST

Non-Patent Literature

Non-Patent Literature 1: The Molecular Probes Handbook.

SUMMARY

It is an object of the present invention to provide a novel non-fluorescent rhodamine dye that produces a similar TICT state in a manner different from such an approach that bonds an aryl group such as N-phenylrhodamines to N atom on the xanthene ring.

As described above, it is suggested that N-phenylrhodamines become non-fluorescent by forming a TICT state in which a xanthene ring-N atom bond is twisted by about 90° in the excited state. The present inventors have focused on a quenching mechanism accompanied by this twist and have considered that non-fluorescence may be achieved by an approach different from introduction of an aryl group into N atom.

Specifically, the present inventors have considered that such a substituent that causes steric hindrance is introduced at an ortho position of a dimethylamino group on the xanthene ring of tetramethylrhodamine (TMR) (FIG. 2(b)), which is a general rhodamine exhibiting strong fluorescence, and a certain amount of twist is imparted in a ground state, so that the formation of the TICT state in the excited state may be promoted and non-fluorescence may be exhibited. As a result of a study using a computational chemical method, a possibility that various molecularly designed compounds may exhibit non-fluorescence due to the TICT state has been suggested. Based on this finding, the present inventors have conducted various studies on a substituent of an amino group on the xanthene ring, a substituent at the ortho position capable of causing steric hindrance with the substituent of the amino group on the xanthene ring, and other substituents and, as a result, have completed the present invention.

In other words, the present invention provides:

[1] a compound represented by the following general formula (I) or a salt thereof.

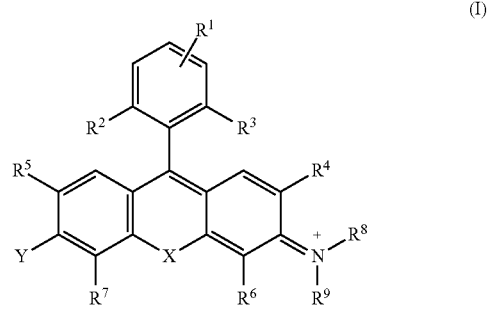

(where:

$R^1$ represents a hydrogen atom or one to three monovalent substituent groups present on a benzene ring, which are the same or different;

$R^2$ and $R^3$ are, each independently, a hydrogen atom or a monovalent substituent group present on a benzene ring;

$R^4$ and $R^5$ are, each independently, a hydrogen atom, a substituted or unsubstituted alkyl group having 1 to 6 carbon atoms, a carboxyl group, an ester group, an amide group, or a halogen atom;

$R^6$ and $R^7$ are, each independently, a hydrogen atom, a substituted or unsubstituted alkyl group having 1 to 6 carbon atoms, a carboxyl group, an ester group, an amide group, or a halogen atom;

provided that any one or more of $R^4$, $R^5$, $R^6$, and $R^7$ are substituents other than a hydrogen atom;

$R^8$ and $R^9$ are, each independently, a hydrogen atom or a substituted or unsubstituted alkyl group having 1 to 14 carbon atoms, $R^8$ and $R^9$ together optionally form a 4-7 membered heterocyclyl containing a nitrogen atom to which $R^8$ and $R^9$ are bonded;

X is selected from an oxygen atom, $Si(R^a)(R^b)$, $C(R^a)(R^b)$, $Ge(R^a)(R^b)$, $P(=O)R^c$, $SO_2$ and Se where:

$R^a$ and $R^b$ are, each independently, an alkyl group having 1 to 6 carbon atoms or an aryl group optionally being substituted, and $R^c$ is an alkyl group having 1 to 6 carbon atoms or a phenyl group optionally being substituted;

Y is —$NR^{10}R^{11}$ or —OH, where:

$R^{10}$ and $R^{11}$ are, each independently, a hydrogen atom or a substituted or unsubstituted alkyl group having 1 to 14 carbon atoms, $R^{10}$ and $R^{11}$ together optionally form a 4-7 membered heterocyclyl containing a nitrogen atom to which $R^{10}$ and $R^{11}$ are bonded;

(i) when Y is —$NR^{10}R^{11}$, in any one or more of a pair of $R^8$ and $R^9$ and a pair of $R^{10}$ and $R^{11}$, two groups constituting the pair are both substituents other than a hydrogen atom, where:

(a) when the two groups constituting the pair of $R^8$ and $R^9$ are both substituents other than a hydrogen atom and at least one group constituting the pair of $R^{10}$ and $R^{11}$ is a hydrogen atom, any one or more of $R^4$ and $R^6$ are substituents other than a hydrogen atom, (b) when the two groups constituting the pair of $R^{10}$ and $R^{11}$ are both substituents other than a hydrogen atom and at least one group constituting the pair of $R^9$ and $R^9$ is a hydrogen atom, any one or more of $R^5$ and $R^7$ are substituents other than a hydrogen atom, (c) when $R^8$, $R^9$, $R^{10}$, and $R^{11}$ are all substituents other than a hydrogen atom, any one or more of $R^4$, $R^5$, $R^6$, and $R^7$ are substituents other than a hydrogen atom; and (2) when Y is —OH, $R^8$ and $R^9$ are both substituents other than a hydrogen atom, and any one or more of $R^4$ and $R^6$ are substituted or unsubstituted alkyl groups having 1 to 6 carbon atoms or a halogen atom.)

[2] The compound or salt thereof according to [1], wherein Y is —$NR^{10}R^{11}$.

[3] The compound or salt thereof according to [2], wherein in any one of the pair of $R^8$ and $R^9$ and the pair of $R^{10}$ and $R^{11}$, all groups are substituents other than a hydrogen atom.

[4] The compound or salt thereof according to [2], wherein in both the pair of $R^8$ and $R^9$ and the pair of $R^{10}$ and $R^{11}$, all groups are substituents other than a hydrogen atom.

[5] The compound or salt thereof according to [4], wherein any one or more of $R^4$ and $R^5$ are substituents other than a hydrogen atom, and any one or more of $R^6$ and $R^7$ are substituents other than a hydrogen atom.

[6] The compound or salt thereof according to any one of [2] to [5], wherein $R^8$, $R^9$, $R^{10}$ and $R^{11}$ are substituted or unsubstituted alkyl groups having 1 to 6 carbon atoms, which are the same or different, any one or more of $R^4$ and $R^6$ and/or any one or more of $R^5$ and $R^7$ are substituents other than a hydrogen atom, and at least one of the alkyl groups of $R^8$, $R^9$, $R^{10}$, and $R^{11}$ is an alkyl group substituted with a hydroxyl group or an alkoxy group.

[7] The compound or salt thereof according to [3], wherein in any one of the pair of $R^8$ and $R^9$ and the pair of $R^{10}$ and $R^{11}$, all groups are substituted or unsubstituted alkyl groups having 1 to 6 carbon atoms, which are the same or different, and at least one of the alkyl groups is an alkyl group substituted with a hydroxyl group or an alkoxy group.

[8] A fluorescent probe for detecting P450 activity comprising the compound or salt thereof according to any one of [1] to [7].

[9] A method of detecting P450 in a cell, comprising:

(a) introducing the fluorescent probe according to [8] into the cell; and, (b) measuring fluorescence emitted in the cell by the fluorescent probe.

According to the present invention, it is possible to provide a novel non-fluorescent rhodamine dye that produces a TICT state.

BRIEF DESCRIPTION OF THE DRAWINGS

FIG. 1 illustrates chemical structures of various rhodamine dyes.

FIG. 2 is a conceptual diagram of study of the present invention.

FIG. 3 illustrates optimized structures of TMR, 4-Cl TMR, and 4,5-diCl TMR in $S_0$(a) and $S_1$(b) states calculated by B3LYP/6-31G*.

FIG. 4 illustrates chemical structures and optical properties of tetramethylrhodamine (TMR), 4-Cl TMR and 4,5-diCl TMR.

FIG. 5 illustrates optical properties of 4-Cl TMR in various solvents.

FIG. 6 illustrates chemical structures and optical properties of 2-Cl TMR, 2-Me TMR and 2-F TMR.

FIG. 7 illustrates optical properties of 2-Cl triMe rhodamine.

FIG. 8 illustrates a chemical structure and an absorption spectrum of Dabcyl.

FIG. 9 illustrates chemical structures and normalized absorption spectra of BHQ1, BHQ2 and BHQ3.

FIG. 10 illustrates chemical structures of QSY7, QSY9, QSY21 and QSY35 and normalized absorption spectra of QSY35, QSY7 and QSY21.

FIG. 11 illustrates chemical structures and optical properties of 4-Cl TMSiR and 4,5-diCl TMSiR.

FIG. 12 illustrates a design strategy of a P450 active fluorescent probe in the present invention.

FIG. 13 illustrates time-dependent fluorescence changes of rhodamine derivatives using 11 types of P450 subtypes.

FIG. 14 illustrates time-dependent fluorescence changes of Compounds 23 to 26 using 11 types of P450 subtypes.

FIG. 16 illustrates absorption/fluorescence spectrum changes when Compound 29 is reacted with CYP3A4.

FIG. 17 illustrates time-dependent fluorescence changes of Compound 29 using human liver microsomes and NADPH producing system.

FIG. 18 illustrates fluorescence imaging of differentiated HepaRG using Compound 29.

FIG. 19 shows a box plot illustrating a distribution of fluorescence intensity of 20 cells selected from each group in the experiment of FIG. 18.

FIG. 20 shows the HPLC chromatogram after purification of Compound 16.

FIG. 21 shows the HPLC chromatogram after purification of Compound 23.

FIG. 22 shows the HPLC chromatogram after purification of Compound 24.

FIG. 23 shows the HPLC chromatogram after purification of Compound 25.

FIG. 24 shows the HPLC chromatogram after purification of Compound 26.

FIG. 25 shows the HPLC chromatogram after purification of Compound 27.

DETAILED DESCRIPTION

Figure 15:
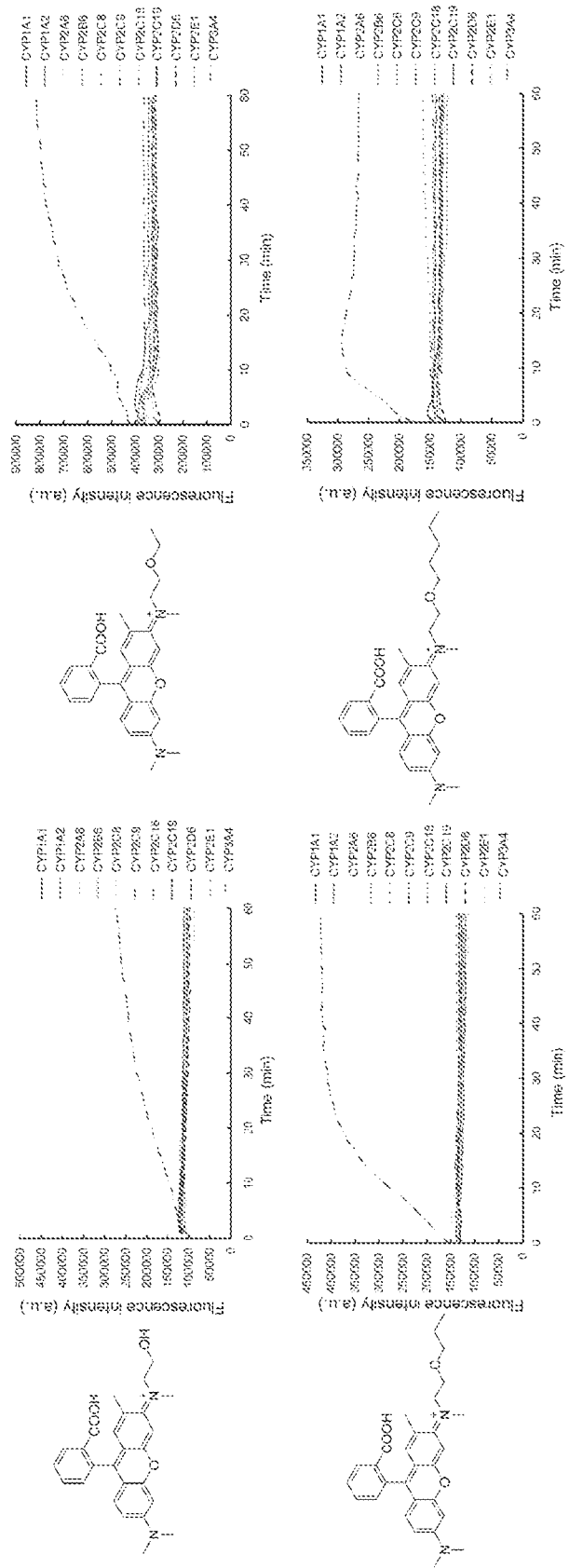
FIG. 15 illustrates time-dependent fluorescence changes of rhodamine derivatives using 11 types of P450 subtypes.

In the present specification, unless otherwise noted, "alkyl group" or an alkyl moiety of a substituent (e.g., alkoxy group) containing the alkyl moiety refers to an alkyl group including a straight chain, branched chain, ring, or combination thereof having, for example, carbon atoms of 1 to 14, preferably carbon atoms of 1 to 12, more preferably carbon atoms of about 1 to 6. When the carbon number is designated, the alkyl means "alkyl" having carbon atoms in a range of the number. More specifically, examples of the alkyl group include a methyl group, ethyl group, n-propyl group, isopropyl group, cyclopropyl group, n-butyl group, sec-butyl group, isobutyl group, tert-butyl group, cyclopropylmethyl group, n-pentyl group, and n-hexyl group.

In the present specification, the term "halogen atom" may be a fluorine atom, chlorine atom, bromine atom, or iodine atom, and is preferably a fluorine atom, chlorine atom, or bromine atom.

1. Compound Represented by General Formula (I) or Salt Thereof

One embodiment of the present invention is a compound represented by the following general formula (I), or salt thereof.

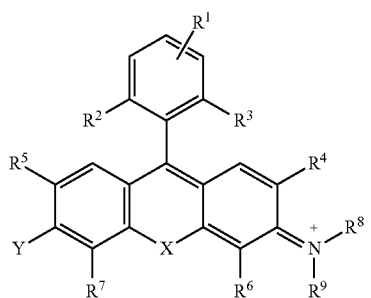

(I)

In general formula (I), $R^1$ is a hydrogen atom or represents one to three monovalent substituent groups present on a benzene ring, which are the same or different.

The type of monovalent substituent group represented by $R^1$ is not particularly limited and is preferably selected from the group consisting of an alkyl group having 1 to 14 carbon atoms (preferably 1 to 12 carbon atoms, more preferably 1 to 6 carbon atoms), an alkenyl group having 1 to 6 carbon atoms, an alkynyl group having 1 to 6 carbon atoms, an alkoxy group having 1 to 14 carbon atoms (preferably 1 to 12 carbon atoms, more preferably 1 to 6 carbon atoms), a hydroxyl group, a carboxy group, a sulfonyl group, an alkoxycarbonyl group, a halogen atom, an amino group, an amide group and an alkylamido group.

These monovalent substituent groups may furthermore have any of one or more substituent groups. For example, one or more halogen atoms, carboxy groups, sulfonyl groups, hydroxyl groups, amino groups, alkoxy groups, or the like may be present in the alkyl group represented by $R^1$, and, for example, the alkyl group represented by $R^1$ may be an alkyl halide group, a hydroxyalkyl group, a carboxyalkyl group, an aminoalkyl group, or the like.

Also, one or two alkyl groups may be present in the amino group represented by $R^1$, and the amino group represented by $R^1$ may be a monoalkyl amino group or a dialkyl amino group. Furthermore, in the case that the alkoxy group represented by $R^1$ has a substituent group, examples thereof include a carboxy-substituted alkoxy group and an alkoxy-carbonyl-substituted alkoxy group, and more specific examples include a 4-carboxybutoxy group and a 4-acetoxymethyloxycarbonylbutoxy group.

Also, one or two alkyl groups may be present in the amide group, alkylamido group, sulfonyl group or alkoxycarbonyl group represented by $R^1$, for example.

In a preferred aspect of the present invention, each $R^1$ is a hydrogen atom.

In general formula (I), $R^2$ and $R^3$ are, each independently, a hydrogen atom or a monovalent substituent present on a benzene ring.

The monovalent substituents of $R^2$ and $R^3$ are preferably selected from an alkyl group having 1 to 6 carbon atoms, an alkoxy group having 1 to 6 carbon atoms, a carboxyl group and an ester group.

When $R^2$ and $R^3$ represent an alkyl group, one or more halogen atoms, sulfonyl groups, alkoxy groups, or the like may be present in the alkyl group.

In general formula (I), $R^4$ and $R^5$ are, each independently, a hydrogen atom, a substituted or unsubstituted alkyl group having 1 to 6 carbon atoms, a carboxyl group (—COOH), an ester group (COOR), an amide group (CONR) or a halogen atom (R is an alkyl group).

Examples of the substituent of the alkyl group of $R^4$ or $R^5$ include a halogen atom, a carboxy group, a sulfonyl group, a hydroxyl group, an amino group, and an alkoxy group, and one or two or more of these may be present. Examples of the substituted alkyl group represented by $R^4$ or $R^5$ include a halogenated alkyl group, a hydroxyalkyl group and a carboxyalkyl group.

In general formula (I), $R^6$ and $R^7$ are, each independently, a hydrogen atom, a substituted or unsubstituted alkyl group having 1 to 6 carbon atoms, a carboxyl group (—COOH), an ester group (COOR), an amide group (CONR) or a halogen atom (R is an alkyl group). The details of $R^6$ and $R^7$ are the same as those described for $R^4$ and $R^5$.

In the present invention, it is important that any one or more of $R^4$, $R^5$, $R^6$ and $R^7$ in general formula (I) are substituents other than a hydrogen atom.

Though not intending to be bound by theory, in the present invention, it is considered that a substituent of the amino group on the xanthene ring and a substituent capable of causing steric hindrance are introduced in an ortho position with respect to the amino group, so that a certain amount of twist is imparted in a ground state to promote formation of a TICT state in an excited state, and a compound of general formula (I) exhibits non-fluorescence. The substituent capable of causing steric hindrance is a substituted or unsubstituted alkyl group having 1 to 6 carbon atoms, a carboxyl group (—COOH), an ester group (COOR), an amide group (CONR) or a halogen atom (R is an alkyl group). Preferable examples include a substituted or unsubstituted alkyl group having 1 to 6 carbon atoms or a halogen atom, and more preferable examples include a methyl group, an ethyl group, an i-propyl group, a methyl trifluoride group, a chlorine atom, and a fluoro group.

In general formula (I), X is selected from an oxygen atom, $Si(R^a)(R^b)$, $C(R^a)(R^b)$, $Ge(R^a)(R^b)$, $P(=O)R^c$, $SO_2$, and Se.

In a preferred aspect of the present invention, X is an oxygen atom or $Si(R^a)(R^b)$.

$R^a$ and $R^b$ are, each independently, an alkyl group having 1 to 6 carbon atoms or an aryl group optionally being substituted. $R^a$ and $R^b$ are, independently, preferably an alkyl group having 1 to 3 carbon atoms, and it is more preferable that $R^a$ and $R^b$ both be methyl groups.

One or more halogen atoms, carboxy groups, sulfonyl groups, hydroxyl groups, amino groups, alkoxy groups, or the like may be present in the alkyl group represented by $R^a$ and $R^b$, and, for example, the alkyl group represented by $R^a$ and $R^b$ may be an alkyl halide group, a hydroxyalkyl group, a carboxyalkyl group, or the like.

When $R^a$ and $R^b$ represent an aryl group, the aryl group may be a monocyclic aromatic group or condensed aromatic group, and the aryl ring may include one or more ring-structured heteroatoms (e.g., nitrogen atom, oxygen atom, sulfur atom, or the like). A phenyl group is preferred as the aryl group. One or more substituent groups may be present on the aryl ring. One or more substituent groups such as a halogen atom, carboxy group, sulfonyl group, hydroxyl group, amino group, alkoxy group, or the like may be present.

$R^c$ is an alkyl group having 1 to 6 carbon atoms or a phenyl group optionally being substituted. Examples of the substituent of the phenyl group include a methyl group, a hydroxy group and a methoxy group.

From the viewpoint of easy introduction in synthesis, $R^c$ is preferably a methyl group or a phenyl group. It is more preferable that $R^c$ be a methyl group because water solubility is higher.

$R^8$ and $R^9$ are, each independently, a hydrogen atom or a substituted or unsubstituted alkyl group having 1 to 14 carbon atoms, preferably 1 to 12 carbon atoms, and more preferably 1 to 6 carbon atoms.

Examples of substituent groups of the alkyl group include halogen atom, carboxy group, sulfonyl group, hydroxyl group, amino group, and alkoxy group.

$R^8$ and $R^9$ together may form a 4-7 membered (preferably 5-membered) heterocyclyl containing a nitrogen atom to which $R^8$ and $R^9$ are bonded.

In general formula (I), Y is —$NR^{10}R^{11}$ or —OH.

When Y is —$NR^{10}R^{11}$, a compound of general formula (I) can be represented by the following formula.

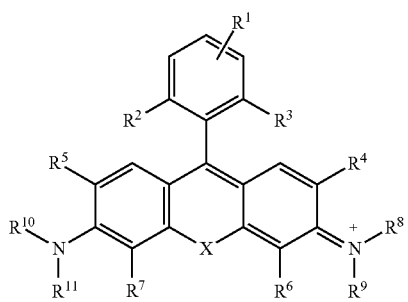

(II)

In general formulas (I) and (II), $R^{10}$ and $R^{11}$ are, each independently, a hydrogen atom or a substituted or unsubstituted alkyl group having 1 to 14 carbon atoms, preferably 1 to 12 carbon atoms, and more preferably 1 to 6 carbon atoms.

Examples of substituent groups of the alkyl group include halogen atom, carboxy group, sulfonyl group, hydroxyl group, amino group, and alkoxy group.

$R^{10}$ and $R^{11}$ together may form a 4-7 membered (preferably 5-membered) heterocyclyl containing a nitrogen atom to which $R^{10}$ and $R^{11}$ are bonded.

In general formula (I), when Y is —$NR^{10}R^{11}$, in any one or more of a pair of $R^8$ and $R^9$ and a pair of $R^{10}$ and $R^{11}$, two groups constituting the pair are both substituents other than a hydrogen atom.

Here, (a) when two groups constituting the pair of $R^8$ and $R^9$ are both substituents other than a hydrogen atom, and at least one group constituting the pair of $R^{10}$ and $R^{11}$ is a hydrogen atom, any one or more of $R^4$ and $R^6$ are substituents other than a hydrogen atom.

(b) When two groups constituting the pair of $R^{10}$ and $R^{11}$ are both substituents other than a hydrogen atom, and at least one group constituting the pair of $R^8$ and $R^9$ is a hydrogen atom, any one or more of $R^5$ and $R^7$ are substituents other than a hydrogen atom.

(c) When $R^8$, $R^9$, $R^{10}$ and $R^{11}$ are all substituents other than a hydrogen atom, any one or more of $R^4$, $R^5$, $R^6$ and $R^7$ are substituents other than a hydrogen atom.

In the present invention, it is important that in general formula (I), when Y is —$NR^{10}R^{11}$, molecular design is performed so that at least one of the pair of $R^8$ and $R^9$ and the pair of $R^{10}$ and $R^{11}$ which are substituents of the amino group on the xanthene ring cause steric hindrance with substituents at their ortho positions. It is considered that by performing the molecular design in this way, a certain amount of twist is imparted in the ground state to promote the formation of the TICT state in the excited state, and the compound of general formula (I) exhibits non-fluorescence.

In one preferred embodiment of the present invention, in general formula (I), in both the pair of $R^8$ and $R^9$ and the pair of $R^{10}$ and $R^{11}$, any group constituting these pairs is a substituent other than a hydrogen atom, and any one or more of $R^4$, $R^5$, $R^6$ and $R^7$ are substituents other than a hydrogen atom.

In another preferred embodiment of the present invention, in general formula (I), in both the pair of $R^8$ and $R^9$ and the pair of $R^{10}$ and $R^{11}$, any group constituting these pairs is a substituent other than a hydrogen atom, any one or more of $R^4$ and $R^5$ are substituents other than a hydrogen atom, and any one or more of $R^6$ and $R^7$ are substituents other than a hydrogen atom.

In this embodiment, in both amino groups on the xanthene ring, a steric hindrance is caused between the substituent of the amino group and the substituent at the ortho position with respect to each amino group, and the level of non-fluorescence becomes very high, allowing it to be used as an excellent quenching group.

In another preferred embodiment of the present invention, in general formula (I), in any one of the pair of $R^8$ and $R^9$ and the pair of $R^{10}$ and $R^{11}$, any group that constitutes the pair (i.e., $R^8$ and $R^9$, or $R^{10}$ and $R^{11}$) are also substituents other than hydrogen atom. In this case, (a) when two groups constituting the pair of $R^8$ and $R^9$ are both substituents other than a hydrogen atom, any one or more of $R^4$ and $R^6$ are substituents other than a hydrogen atom, and when two groups constituting the pair of $R^{10}$ and $R^{11}$ are both substituents other than a hydrogen atom, any one or more of $R^5$ and $R^7$ are substituents other than a hydrogen atom.

In this embodiment, in one of the amino groups on the xanthene ring a steric hindrance is caused between the substituent of the amino group and the substituent at the ortho position with respect to the amino group.

Such an embodiment has a high non-fluorescent level, and also, for example, acts P450 to remove the alkyl group on the amino group due to its N-dealkylation activity, so that relief of steric hindrance occurs, and in such a case of recovering the fluorescence, this embodiment can be effectively used for detecting P450 because there is one reaction point.

In a preferred aspect of the present invention, in general formula (I), $R^8$, $R^9$, $R^{10}$ and $R^{11}$ are substituted or unsubstituted alkyl groups having 1 to 6 carbon atoms, which are the same or different, any one or more of $R^4$ and $R^6$ and/or any one or more of $R^5$ and $R^7$ are substituents other than a hydrogen atom, that is, substituted or unsubstituted alkyl groups having 1 to 6 carbon atoms, halogen atoms, carboxyl groups (—COOH), ester groups (COOR), amide groups (CONR) or halogen atoms (R is an alkyl group), preferably substituted or unsubstituted alkyl groups having 1 to 6 carbon atoms or halogen atoms, and more preferably methyl groups, ethyl groups, i-propyl groups, methyl trifluoride groups, chlorine atoms, fluorine atoms, or the like.

Here, the substituted or unsubstituted alkyl group for $R^8$, $R^9$, $R^{10}$ and $R^{11}$ is preferably a methyl group, an ethyl group, or a propyl group.

Further, $R^8$ and $R^9$ and/or $R^{10}$ and $R^{11}$ together may form a 4-7 membered (preferably 5-membered) heterocyclyl containing a nitrogen atom to which $R^8$ and $R^9$, or $R^{10}$ and $R^{11}$ are bonded.

In another preferred aspect of the present invention, in general formula (I), Y is —$NR^{10}R^{11}$, $R^8$, $R^9$, $R^{10}$ and $R^{11}$ are substituted or unsubstituted alkyl groups having 1 to 6 carbon atoms, which are the same or different, any one or more of $R^4$ and $R^6$ and/or any one or more of $R^5$ and $R^7$ are substituents other than a hydrogen atom, and at least one of the alkyl groups of $R^8$, $R^9$, $R^{10}$ and $R^{11}$ is an alkyl group substituted with a hydroxyl group.

In this case, at least one of substituents at the ortho position with respect to the amino group on the xanthene ring to which the alkyl group substituted with a hydroxyl group is bonded (that is, the substituent means $R^4$ and $R^6$ when $R^8$ and/or $R^9$ is an alkyl group substituted with a hydroxyl group, and means $R^5$ and $R^7$ when $R^{10}$ and/or $R^{11}$ is an alkyl group substituted with a hydroxyl group) is preferably a substituent other than a hydrogen atom. Similarly to the above, the substituent other than a hydrogen atom is a substituted or unsubstituted alkyl group having 1 to 6 carbon atoms, a halogen atom, a carboxyl group (—COOH), an ester group (COOR), an amide group (CONR) or a halogen atom (R is an alkyl group), preferably a substituted or unsubstituted alkyl group having 1 to 6 carbon atoms or a halogen atom, and more preferably a methyl group, an ethyl group, an i-propyl group, a methyl trifluoride group, a chlorine atom, a fluorine atom, or the like.

Examples of the alkyl group substituted with a hydroxyl group include, but are not limited to, a hydroxyethyl group.

Among $R^8$, $R^9$, $R^{10}$ and $R^{11}$, alkyl groups other than the alkyl group substituted with a hydroxyl group may be unsubstituted or substituted. The unsubstituted alkyl group is preferably a methyl group, an ethyl group, or a propyl group.

In the case where at least one of the alkyl groups of $R^8$, $R^9$, $R^{10}$ and $R^{11}$ is an alkyl group substituted with a hydroxyl group, depending on the combination of the other part of the structure of the compound of the present invention (a substituent at the ortho position, a substituent of the benzene ring bonded to the xanthene skeleton, etc.), non-fluorescent rhodamine may exhibit selectivity with respect to CYP3A among main P450 molecular species, which is preferable.

In another preferred aspect of the present invention, in general formula (I), Y is —$NR^{10}R^{11}$, $R^8$, $R^9$, $R^{10}$ and $R^{11}$ are substituted or unsubstituted alkyl groups having 1 to 6 carbon atoms, which are the same or different, any one or more of $R^4$ and $R^6$ and/or any one or more of $R^5$ and $R^7$ are substituents other than a hydrogen atom, and at least one of the alkyl groups of $R^8$, $R^9$, $R^{10}$ and $R^{11}$ is an alkyl group substituted with an alkoxy group (alkoxyalkyl group).

In this case, at least one of substituents at the ortho position with respect to the amino group on the xanthene ring to which the alkyl group substituted with an alkoxy group is bonded (that is, the substituent means $R^4$ and $R^6$ when $R^8$ and/or $R^9$ is an alkyl group substituted with an alkoxy group, and means $R^5$ and $R^7$ when $R^{10}$ and/or $R^{11}$ is an alkyl group substituted with an alkoxy group) is preferably a substituent other than a hydrogen atom. Similarly to the above, the substituent other than a hydrogen atom is a substituted or unsubstituted alkyl group having 1 to 6 carbon atoms, a halogen atom, a carboxyl group (—COOH), an ester group (COOR), an amide group (CONR) or a halogen atom (R is an alkyl group), preferably a substituted or unsubstituted alkyl group having 1 to 6 carbon atoms or a halogen atom, and more preferably a methyl group, an ethyl group, an i-propyl group, a methyl trifluoride group, a chlorine atom, a fluorine atom, or the like.

Among $R^8$, $R^9$, $R^{10}$ and $R^{11}$, alkyl groups other than the alkyl group substituted with an alkoxy group may be unsubstituted or substituted. The unsubstituted alkyl group is preferably a methyl group, an ethyl group, or a propyl group.

The total number of carbon atoms of the alkyl group substituted with an alkoxy group is 2 to 12, preferably 2 to 10.

Examples of the alkyl group substituted with an alkoxy group include, but are not limited to, a methoxyethyl group, an ethoxyethyl group, a propoxyethyl group, a butoxyethyl group, and a pentaxyethyl group.

In the case where at least one of the alkyl groups of $R^8$, $R^9$, $R^{10}$ and $R^{11}$ is an alkyl group substituted with an alkoxy group, depending on the combination of the other part of the structure of the compound of the present invention (a substituent at the ortho position, a substituent of the benzene ring bonded to the xanthene skeleton, etc.), non-fluorescent rhodamine may exhibit selectivity with respect to CYP3A among main P450 molecular species, which is preferable.

In another preferred aspect of the present invention, in general formula (I), in any one of the pair of $R^8$ and $R^9$ and the pair of $R^{10}$ and $R^{11}$, all groups are substituted or unsubstituted alkyl groups having 1 to 6 carbon atoms, which are the same or different, and at least one of the alkyl groups is an alkyl group substituted with a hydroxyl group or an alkoxy group.

Here, when $R^8$ and $R^9$ are both the same or different substituted or unsubstituted alkyl groups having 1 to 6 carbon atoms, any one or more of $R^4$ and $R^6$ are substituted or unsubstituted alkyl groups having 1 to 6 carbon atoms, carboxyl groups (—COOH), ester groups (COOR), amide groups (CONR) or halogen atoms (R is an alkyl group), preferably substituted or unsubstituted alkyl groups having 1 to 6 carbon atoms or halogen atoms, and more preferably methyl groups, ethyl groups, i-propyl groups, methyl trifluoride groups, chlorine atoms, fluoro groups, or the like.

Further, when $R^{10}$ and $R^{11}$ are both the same or different substituted or unsubstituted alkyl groups having 1 to 6 carbon atoms, any one or more of $R^5$ and $R^7$ are substituted or unsubstituted alkyl groups having 1 to 6 carbon atoms, carboxyl groups (—COOH), ester groups (COOR), amide groups (CONR) or halogen atoms (R is an alkyl group). Preferable examples include a substituted or unsubstituted alkyl group having 1 to 6 carbon atoms or a halogen atom, and more preferable examples include a methyl group, an ethyl group, an i-propyl group, a methyl trifluoride group, a chlorine atom, and a fluoro group.

Here, among substituted or unsubstituted alkyl groups having 1 to 14 carbon atoms of $R^8$, $R^9$, $R^{10}$ and $R^{11}$, alkyl groups other than the alkyl group substituted with a hydroxyl group or an alkoxy group may be unsubstituted or substituted. The unsubstituted alkyl group is preferably a methyl group, an ethyl group, or a propyl group.

In another preferred aspect of the present invention, in general formula (I), in any one of the pair of $R^8$ and $R^9$ and the pair of $R^{10}$ and $R^{11}$, $R^8$ and $R^9$ or $R^{10}$ and $R^{11}$ are both substituted or unsubstituted alkyl groups having 1 to 6 carbon atoms, which are the same or different.

Here, when $R^8$ and $R^9$ are both the same or different substituted or unsubstituted alkyl groups having 1 to 6 carbon atoms, any one or more of $R^4$ and $R^6$ are substituted or unsubstituted alkyl groups having 1 to 6 carbon atoms, carboxyl groups (—COOH), ester groups (COOR), amide groups (CONR) or halogen atoms (R is an alkyl group), preferably substituted or unsubstituted alkyl groups having 1 to 6 carbon atoms or halogen atoms, and more preferably methyl groups, ethyl groups, i-propyl groups, methyl trifluoride groups, chlorine atoms, fluoro groups, or the like.

Further, when $R^{10}$ and $R^{11}$ are both the same or different substituted or unsubstituted alkyl groups having 1 to 6 carbon atoms, any one or more of $R^5$ and $R^7$ are substituted or unsubstituted alkyl groups having 1 to 6 carbon atoms, carboxyl groups (—COOH), ester groups (COOR), amide groups (CONR) or halogen atoms (R is an alkyl group). Preferable examples include a substituted or unsubstituted alkyl group having 1 to 6 carbon atoms or a halogen atom, and more preferable examples include a methyl group, an ethyl group, an i-propyl group, a methyl trifluoride group, a chlorine atom, and a fluoro group.

Here, the substituted or unsubstituted alkyl group for $R^8$, $R^9$, $R^{10}$ and $R^{11}$ is preferably a methyl group, an ethyl group, or a propyl group.

Further, $R^8$ and $R^9$ and/or $R^{10}$ and $R^{11}$ together may form a 4-7 membered (preferably 5-membered) heterocyclyl containing a nitrogen atom to which $R^8$ and $R^9$, or $R^{10}$ and $R^{11}$ are bonded.

In general formula (I), when Y is —OH, a compound of general formula (I) can be represented by the following formula.

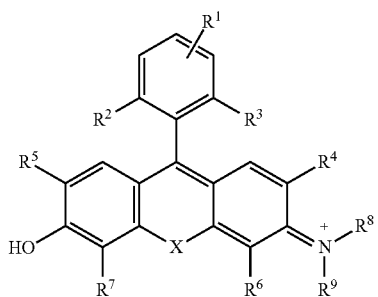

(III)

In general formula (I), when Y is —OH, $R^8$ and $R^9$ are both substituents other than a hydrogen atom, and any one or more of $R^4$ and $R^6$ are substituted or unsubstituted alkyl groups having 1 to 6 carbon atoms, carboxyl groups (—COOH), ester groups (COOR), amide groups (CONR) or halogen atoms (R is an alkyl group). Preferred is a substituted or unsubstituted alkyl group having 1 to 6 carbon atoms or a halogen atom.)

In a preferred aspect of the present invention, in general formula (III), $R^8$ and $R^9$ are both substituted or unsubstituted alkyl groups having 1 to 6 carbon atoms, which are the same or different, and any one or more of $R^4$ and $R^6$ are substituted or unsubstituted alkyl groups having 1 to 6 carbon atoms, carboxyl groups (—COOH), ester groups (COOR), amide groups (CONR) or halogen atoms (R is an alkyl group), preferably substituted or unsubstituted alkyl groups having 1 to 6 carbon atoms or halogen atoms, and more preferably methyl groups, ethyl groups, i-propyl groups, methyl trifluoride groups, chlorine atoms, fluoro groups, or the like.

Here, the substituted or unsubstituted alkyl group for $R^8$ and $R^9$ is preferably a methyl group, an ethyl group, or a propyl group.

The compounds of general formulas (I) to (III) of the present invention can exist as acid addition salts or base addition salts. Examples of the acid addition salt include mineral acid salts such as hydrochlorides, sulfates and nitrates, and organic acid salts such as methanesulfonate, p-toluenesulfonate, oxalate, citrate and tartrate. Examples of the base addition salt include metal salts such as sodium salt, potassium salt, calcium salt and magnesium salt, ammonium salt, and organic amine salts such as triethylamine salt. In addition to these, there are also cases in which salts form with an amino acid such as glycine. Compounds or salts thereof of general formulas (I) to (III) of the present invention can also exist as hydrates or solvates, but these substances are also within the scope of the present invention.

The compounds of general formulas (I) to (III) of the present invention sometimes have one or more asymmetrical carbons, depending on the types of substituents. In addition to optical isomers based on one or more asymmetrical carbons and stereoisomers such as diastereomers based on two or more asymmetrical carbons, any mixtures of stereoisomers, racemates, etc., are all encompassed within the scope of the present invention.

Methods for producing representative compounds of compounds of general formulas (I) to (III) of the present invention are specifically shown in the examples in the present specification. Therefore, one skilled in the art can produce compounds represented by general formulas (I) to (III) by appropriately selecting the reaction raw materials, reaction conditions, reaction reagents, etc. based on these explanations and modifying or changing these methods as needed.

The followings are non-limiting examples of the compound or salts thereof of the present invention.

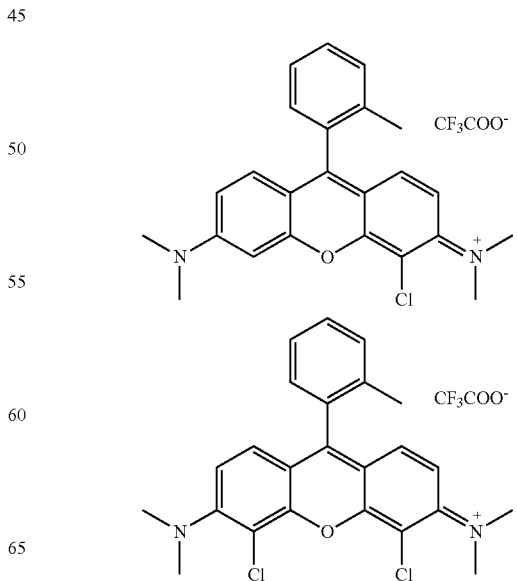

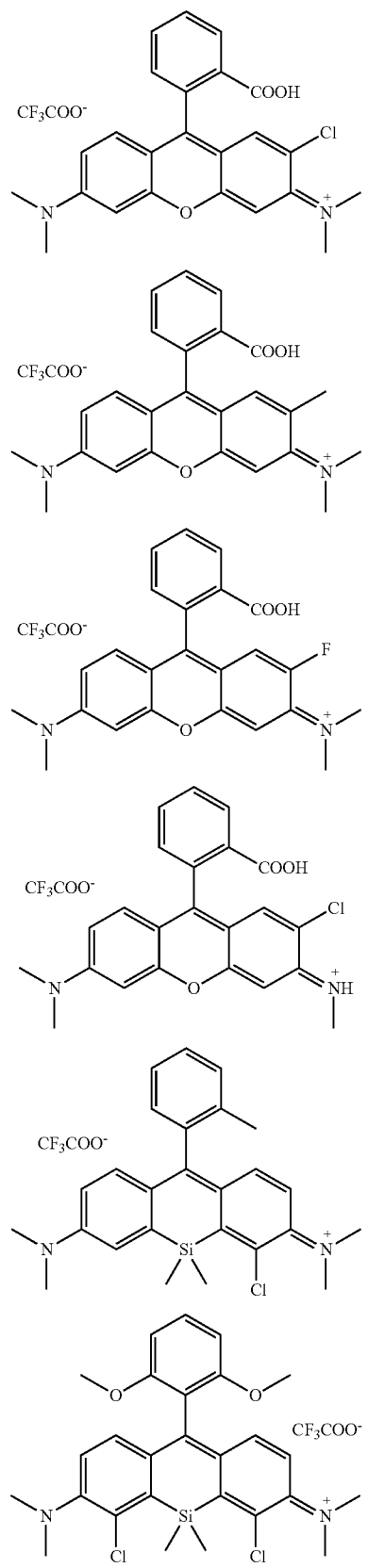
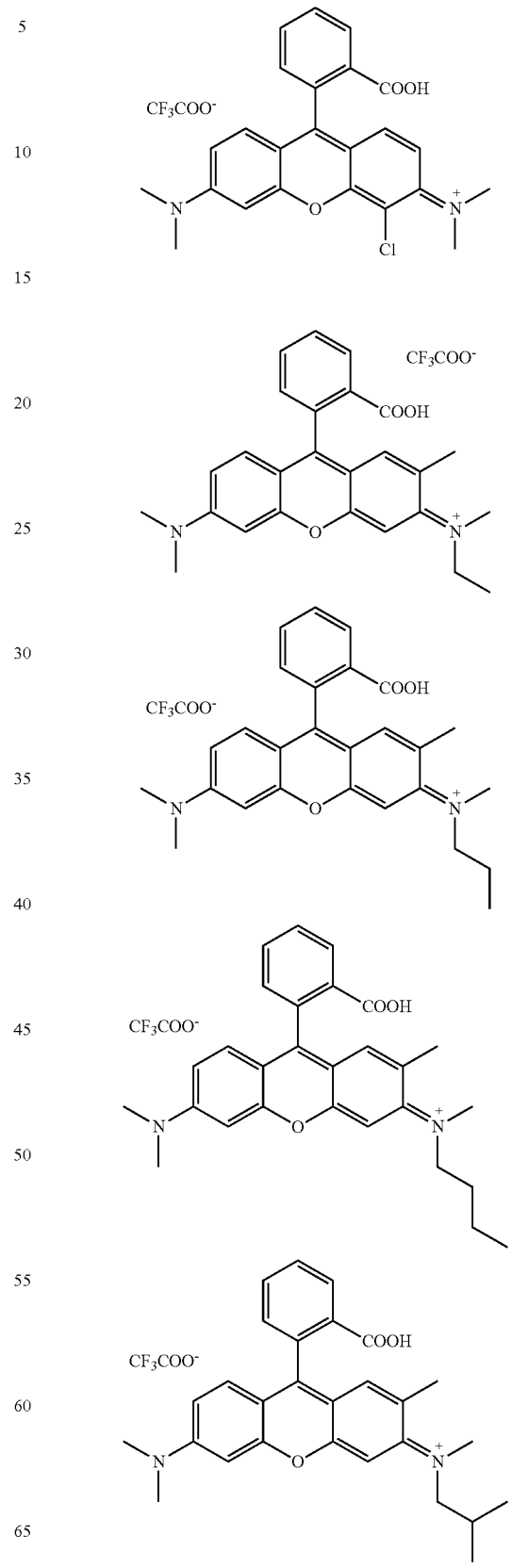

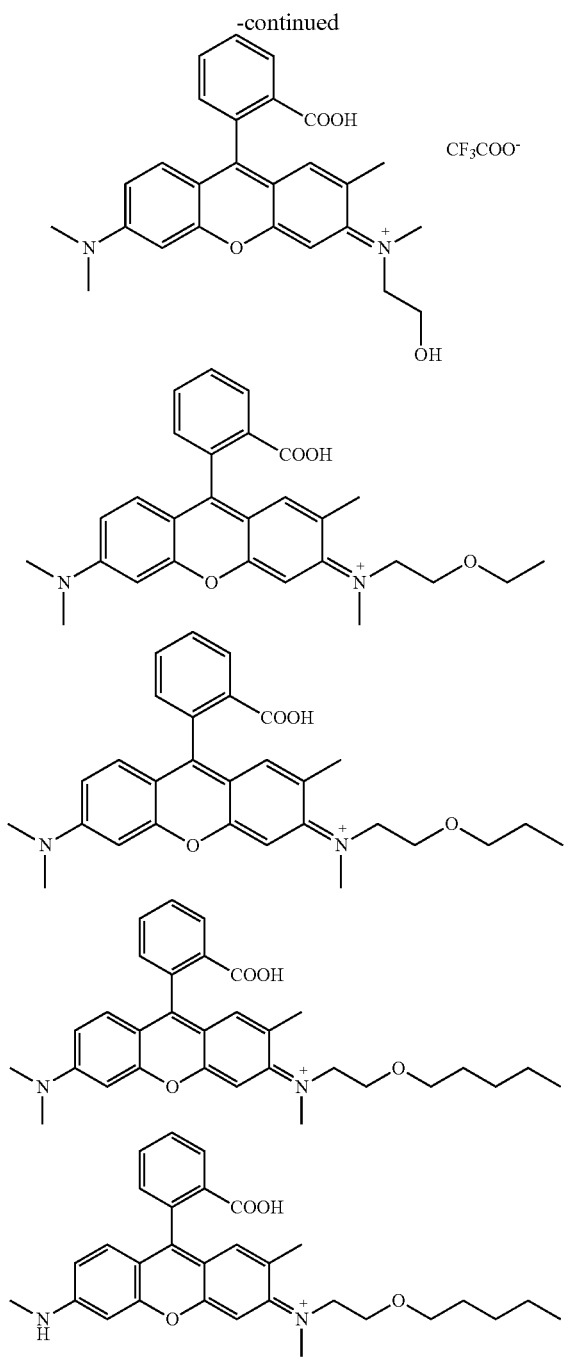

2. Fluorescent Probe for Detecting Cytochrome P450 Activity

One more embodiment of the present invention is a fluorescent probe for detecting P450 activity that includes the compounds of general formulas (I) to (III) or salts thereof.

Cytochrome P450 is a metabolic enzyme responsible for the redox reaction in a phase I reaction of drug metabolism, and plays an important role in elimination of the drug from the body. Usually, most of the drugs that have entered the body become highly water-soluble compounds in the liver by metabolic enzymes including P450 and are excreted out of the body. On the other hand, many drugs have effects such as inhibition against specific subtypes of P450 and enzyme induction, and cause drug-drug interactions such as changes in therapeutic effects and occurrence of serious side effects during co-administration of drugs. Therefore, it is extremely important to measure P450 inhibitory and inducing activity of drug candidate compounds at the early stage of drug development.

In the measurement of the P450 inhibitory and the inducing activity in drug development, for example, methods for quantifying metabolites of a P450 substrate such as testosterone and midazolam using LC-MS/MS are used; however, these methods require effort and time for sample adjustment and measurement. On the other hand, a method using a probe that exhibits fluorescence and bioluminescence for the first time when metabolized by a P450 molecular species enables simultaneous measurement of many samples on a multi-well plate and high-throughput measurement of inhibitory action and inducing action against P450 of many drug candidate compounds at the initial stage of drug discovery, so that various fluorescent and bioluminescent substrates have been developed so far. However, most of these probes do not exhibit specificity for a particular P450 subtype, and their use is limited to detecting inhibitory activity against recombinant P450s. Therefore, a probe that is specifically metabolized to a particular subtype and exhibits a fluorescence increase is a useful tool that enables detection of inhibitory and induction effect on P450 in human liver microsomes and living cells.

By the way, most of the existing P450 fluorescence detection probes use O-dealkylation as a fluorescence switching site, and there are very few reports of such fluorescent probes that directly detect N-dealkylation by fluorescence. This is probably because it is more difficult to combine N-dealkylation with a fluorescence change than O-dealkylation.

The compounds of general formulas (I) to (III) of the present invention are considered to exhibit non-fluorescence due to steric hindrance of the alkyl group on N atom and the substituent on the ortho position. Therefore, it is considered that the alkyl group on the amino group is removed due to the N-dealkylation activity of P450 to relieve the steric hindrance and restore the fluorescence, which makes it possible to detect the activity of P450.

The compounds of general formulas (I) to (III) of the present invention can be expected to have high S/N before and after the reaction, and, in addition, since a rhodamine dye itself is a fluorescent dye excellent in terms of water solubility, wavelength length, and cell application, the compounds are expected to become fluorescent probes that exceed the performance of existing probes if a P450 activity detection probe using this nucleus can be developed.

The fluorescent probe for detecting P450 activity of the present invention can be applied to detection of a wide range of P450s. For example, the fluorescent probe can be applied to CYP3A4, CYP3A5, CYP1A1, CYP2C8 and the like.

Here, CYP3A4 is the most major drug-metabolizing enzyme of P450 species present in the human body, and is involved in the metabolism of about 50% of currently clinically used drugs. Therefore, investigating the inhibitory action and inducing action of drugs on CYP3A4 is very important to know the drug-drug interaction, and if a probe that selectively detects the activity of CYP3A4 in living cells can be developed, the probe is expected to become a tool that can detect the drug-drug interactions such as inhibitory and induction of CYP3A4 at the level of living cells. Several reports have been made so far on fluorescent probes with high selectivity for CYP3A. Although 7-benzyloxy-4-trifluoromethylcoumarin (BFC) and 7-benzyloxyquinoline (BQ) are fluorescent probes metabolized by CYP3A, these probes are known to be metabolized to some extent by CYP1A2 (Stresser, D. M.; Turner, S. D.; Blanchard, A. P.; Miller, V. P.; Crespi, C. L. Drug Metab. Dispos. 2002, 30(7), 845-852). Although the patent literature (WO2017/068612) reports the following compound as a CYP3A selective fluorescent probe, its use has so far been limited to studies using a purified P450 enzyme.

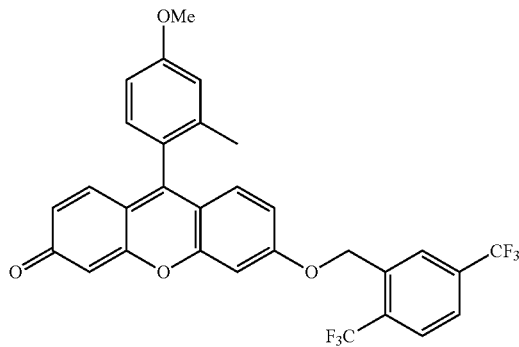 [SMILES: COc1ccc(-c2c3ccc(=O)cc-3oc3cc(OCc4cc(C(F)(F)F)ccc4C(F)(F)F)ccc23)c(C)c1]

Another embodiment of the present invention is a fluorescent probe for detecting P450 activity, preferably fluorescent probe for detecting CYP3A activity, including a compound or salt thereof in which in general formula (I), Y is —NR$^{10}$R$^{11}$, R$^8$, R$^9$, R$^{10}$ and R$^{11}$ are substituted or unsubstituted alkyl groups having 1 to 6 carbon atoms, which are the same or different, any one or more of R$^4$ and R$^6$ and/or any one or more of R$^5$ and R$^7$ are substituents other than a hydrogen atom, and at least one of the alkyl groups of R$^8$, R$^9$, R$^{10}$ and R$^{11}$ is an alkyl group substituted with a hydroxyl group or an alkoxy group.

In the probe, at least one of substituents at the ortho position with respect to the amino group on the xanthene ring to which the alkyl group substituted with a hydroxyl group or an alkoxy group is bonded (that is, the substituent means R$^4$ and R$^6$ when R$^8$ and/or R$^9$ is an alkyl group substituted with a hydroxyl group or an alkoxy group, and means R$^5$ and R$^7$ when R$^{10}$ and/or R$^{11}$ is an alkyl group substituted with a hydroxyl group or an alkoxy group) is preferably a substituent other than a hydrogen atom.

Furthermore, in the probe, among R$^8$, R$^9$, R$^{10}$ and R$^{11}$, alkyl groups other than the alkyl group substituted with an alkoxy group may be unsubstituted or substituted. The unsubstituted alkyl group is preferably a methyl group, an ethyl group, or a propyl group.

The fluorescent probe for detecting CYP3A activity of the present invention is capable of selectively detecting CYP3A, and its utility is high.

One more embodiment of the present invention is a method of detecting P450 in a cell, wherein the method includes (a) introducing the fluorescent probe of the present invention into the cell and (b) measuring fluorescence emitted in the cell by the fluorescent probe.

The method of using the fluorescent probe of the present invention is not particularly limited, and the fluorescent probe can be used in the same manner as conventionally known fluorescent probes. Usually, the compound represented by general formula (I) or salt thereof may be dissolved in an aqueous medium such as physiological saline and buffer, a mixture of the aqueous medium and a water-miseible organic solvent such as ethanol, acetone, ethylene glycol, dimethyl sulfoxide, and dimethylformamide, or the like, this solution may be added to an appropriate buffer containing cells or tissues, and fluorescence spectrum may be measured. The fluorescent probe of the present invention may be combined with an appropriate additive and used in the form of a composition. For example, it may optionally be combined with additives such as buffers, dissolving aids, and pH adjusting agents.

Hereinafter, the present invention is described by Examples, but the present invention is not limited thereto.

EXAMPLES

[Preliminary Examination]

The present inventors have considered that such a substituent that causes steric hindrance is introduced at an ortho position of a dimethylamino group on the xanthene ring of tetramethylrhodamine (TMR) (FIG. 2(b)), which is a general rhodamine exhibiting strong fluorescence, and a certain amount of twist is imparted in a ground state, so that the formation of the TICT state in the excited state may be promoted and non-fluorescence may be exhibited. Thus, the present inventors first decided to verify this hypothesis using computational chemistry. As illustrated in FIG. 3, in addition to TMR generally known to exhibit strong fluorescence, 4-Cl TMR and 4,5-diCl TMR that caused steric hindrance with the dimethylamino group by substituting a Cl group at the 4-position of the xanthene ring or at the 4,5-position were examined using a computational chemistry method.

Gaussian09 which was commercially available software was used for the molecular orbital calculation, and the basis function was calculated as 6-31G*. After a restable structure in each ground state was calculated, the restable structure in the excited state was calculated by the time-dependent density functional (TD-DFT).

FIG. 3 illustrates most stable structure in the obtained ground state and excited state and orbitals corresponding to HOMO and LUMO. Here, a dihedral angle formed by a plane passing through atoms a, b and c and a plane passing through atoms b, c and d in each structural formula in FIG. 3 is represented by φ. In TMR in which a substituent is not introduced at the ortho position of the dimethylamino group, the dihedral angle φ in the most stable structure in both the ground state and the excited state is almost 0°, indicating that a planar structure is provided.

The orbitals corresponding to HOMO and LUMO are distributed in both the xanthene ring and the dimethylamino group, and it has been supported that when the two orbitals in the excited state sufficiently overlap, the $S_1 \rightarrow S_0$ transition becomes an electronic transition.

Since oscillator strength f which was an index of the likelihood of electronic transition was f=0.49, it was supported by computational chemistry that the $S_1 \rightarrow S_0$ transition became an electronic transition in TMR and exhibited fluorescence.

On the other hand, it was suggested that in 4-Cl TMR and 4,5-diCl TMR in which the Cl group was introduced into the xanthene ring, a dihedral angle was around 35° in the ground state, and an intramolecular twist caused by steric hindrance occurred between the xanthene ring and the dimethylamino group. In addition, in the excited state, a dihedral angle φ was about 90°, which resulted in a stable twist structure in which the xanthene ring and the dimethylamino group were orthogonal to each other. In the excited state, an orbital corresponding to HOMO was localized in the dimethylamino group, and an orbital of LUMO was localized in the xanthene ring site, so that an overlap between the two orbitals became extremely small, and the oscillator strength f was calculated to be 0 in both the compounds. Therefore, it was suggested that these compound did not transit as fluorescence in the $S_1 \to S_0$ transition and returned to the ground state by non-radiative deactivation to become non-fluorescent.

Examination by Derivative Synthesis

From the examination by the computational chemistry described above, it was suggested that the compound designed this time might exhibit non-fluorescence due to the TICT state, and therefore, next, the present inventors decided to actually synthesize these compounds and evaluate their optical properties.

Synthesis Example 1

(1) Synthesis of 3,6-bis(N,N-dimethylamino)xanthene (Compound 1)

Compound 1

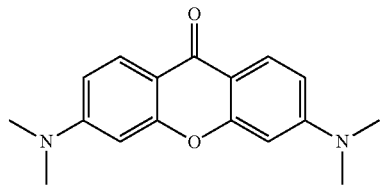

The above Compound 1 was synthesized according to Reference 1 (Kenmoku, S.; Urano, Y.; Kojima, H.; Nagano, T. J. Am. Chem. Soc. 2007, 129 (23), 7313-7318).

(2) Synthesis of tetramethylrhodamine (TMR) (Compound 2)

Compound 2

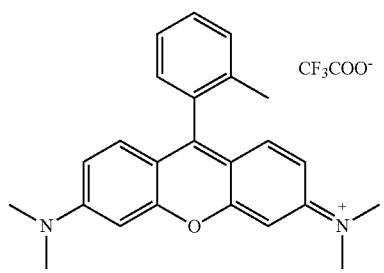

Compound 1 (29.1 mg, 0.10 mmol) was dissolved in tetrahydrofuran (THF) in a two-diameter recovery flask. After argon substitution, o-tolylmagnesium chloride (0.9M THF solution) (6.0 mL, 5.4 mmol) was slowly added under ice cooling, and the mixture was stirred at 60° C. for 70 minutes. 2N hydrochloric acid was added until the reaction solution became acidic, the reaction solution was extracted with $CH_2Cl_2$, and the organic layer was removed under reduced pressure. A residue was purified by HPLC (eluent, A/B=40/60→0/100, 25 minutes; A: $H_2O$ containing 0.1% trifluoroacetic acid (TFA) (v/v), B: MeCN/$H_2O$=80/20 containing 0.1% TFA (v/v)), and further purified by HPLC (eluent, A/B=40/60→0/100, 25 minutes; A: $H_2O$, B: MeCN/$H_2O$=80/20) to obtain Compound 2 (17.2 mg, yield 35%).

$^1$H-NMR (300 MHz, $CDCl_3$) δ 2.04 (s, 3H), 3.38 (s, 12H), 6.90 (d, 2H, J=2.2 Hz), 6.97 (dd, 2H, J=9.5 Hz, 2.2 Hz), 7.15-7.20 (m, 3H), 7.38-7.45 (m, 2H), 7.50-7.54 (m, 1H).

$^{13}$C-NMR (75 MHz, $CDCL_3$) δ 19.5, 41.1, 96.8, 113.5, 114.5, 126.1, 128.7, 130.1, 130.7, 131.3, 131.4, 135.7, 157.4, 157.7, 158.3.

HRMS (ESI$^+$): Calcd for [M]$^+$, 357.1967, Found, 357.1938 (−2.9 mmu).

(3) Synthesis of 4-Cl-3,6-bis(N,N-dimethylamino)xanthone (Compound 3)

Compound 3

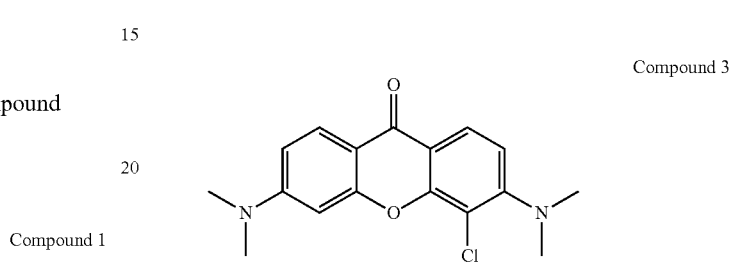

Compound 1 (118.1 mg, 0.42 mmol) was suspended in MeOH (22 mL), and NaOCl.5$H_2O$ (72.6 mg, 0.44 mmol) dissolved in 0.1N NaOHaq. was added under ice cooling with stirring, and the mixture was stirred at room temperature for 12 hours. NaOCl.5$H_2O$ (52.1 mg, 0.32 mmol) was further added, and the mixture was stirred at room temperature for 6 hours. MeOH was removed from the reaction solution under reduced pressure, $H_2O$ was added, and the mixture was extracted with AcOEt. Then, the organic layer was dried over anhydrous $Na_2SO_4$, and the solvent was removed under reduced pressure. A residue was purified by column chromatography (silica gel, hexane/$CH_2Cl_2$=50/50) to give Compound 3 (58.2 mg, yield 30%).

$^1$H-NMR (300 MHz, $CD_2Cl_2$) δ 2.99 (s, 6H), 3.09 (s, 6H), 6.56 (d, 1H, J=2.2 Hz), 6.69 (dd, 1H, J=8.8 Hz, 2.2 Hz), 6.99 (d, 1H, J=8.8 Hz) 8.10. (d, 1H, J=8.8 Hz), 8.12 (d, 1H, J=8.8 Hz).

$^{13}$C-NMR (75 MHz, $CDCl_3$) δ40.2, 43.3, 97.1, 109.7, 111.2, 112.6, 114.3, 117.3, 124.9, 127.7, 153.3, 154.7, 155.1, 158.1, 174.9.

HRMS (ESI$^+$): Calcd for [M+H]$^+$, 317.1057, Found, 317.1072 (+1.5 mmu).

(4) Synthesis of 4-ClTMR (Compound 4)

Compound 4

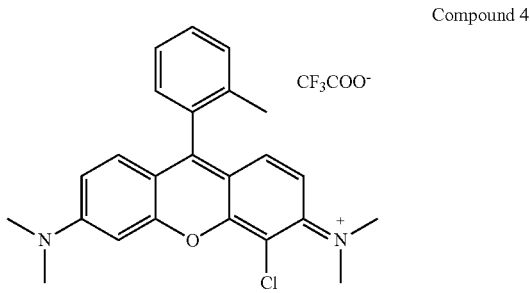

Compound 3 (17.0 mg, 0.05 mmol) was dissolved in THF in a two-diameter recovery flask. After argon substitution, o-tolylmagnesium chloride (0.9M THF solution) (2.8 mL, 2.52 mmol) was slowly added under ice cooling, and the mixture was stirred at 60° C. for 2.5 hours. 2N hydrochloric acid was added until the reaction solution became acidic, the reaction solution was extracted with $CH_2Cl_2$. The organic layer was dried over anhydrous $Na_2SO_4$, and the solvent was removed under reduced pressure. A residue was purified by HPLC (eluent, A/B=80/20→0/100, 20 minutes; A: $H_2O$ containing 0.1% TFA (v/v), B: MeCN/$H_2O$=80/20 containing 0.1% TFA (v/v)) to obtain Compound 4 (24.6 mg, yield 91%).

$^1$H-NMR (300 MHz, $CD_3OD$) δ2.06 (s, 3H), 3.35 (s, 6H), 3.46 (s, 6H), 7.14-7.17 (m, 1H), 7.20-7.31, (m, 5H), 7.45-7.61 (m, 3H).

$^{13}$C-NMR (75 MHz, $CDCl_3$) δ19.7, 41.5, 43.9, 97.9, 108.1, 116.5, 116.6, 117.7, 118.8, 127.3, 129.7, 130.2, 131.5, 132.0, 132.8, 132.9, 137.4, 154.6, 158.3, 159.7, 160.1, 160.3.

HRMS (ESI$^+$): Calcd for [M]$^+$, 391.1577, Found, 391.1607 (+3.0 mmu).

(5) Synthesis of 4,5-diCl-3,6-bis(N,N-dimethylamino)xanthone (Compound 5)

Compound 5

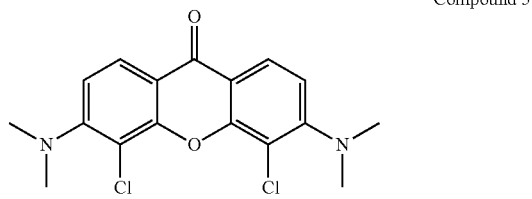

Compound 1 (145 mg, 0.51 mmol) was dissolved in MeOH (5 mL), and NaOCl·5$H_2O$ (469 mg, 2.86 mmol) dissolved in 0.1N NaOHaq. (2.5 mL) was added under ice cooling with stirring, and the mixture was stirred at room temperature for 8 hours. The reaction solution was extracted with AcOEt and washed with saturated $NaHCO_3$aq. Then, the organic layer was dried over anhydrous $Na_2SO_4$, and the solvent was removed under reduced pressure. A residue was purified by column chromatography (silica gel, hexane/$CH_2Cl_2$=10/90) to give Compound 5 (93 mg, yield 52%).

$^1$H-NMR (300 MHz, $CD_2Cl_2$) δ3.28 (s, 12H), 7.29 (d, 2H, J=8.8 Hz), 8.29 (d, 2H, J=8.8 Hz).

$^{13}$C-NMR (100 MHz, $CD_2Cl_2$) 643.4, 112.7, 115.4, 116.5, 125.1, 153.8, 156.1, 174.9.

HRMS (ESI$^+$): Calcd for [M]$^+$, 351.0667, Found, 351.0620 (−4.7 mmu).

(6) Synthesis of 4,5-diClTMR (Compound 6)

Compound 6

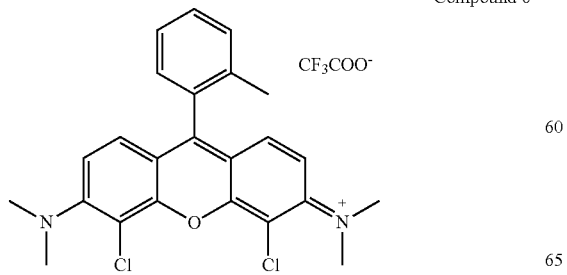

Compound 5 (18.8 mg, 0.05 mmol) was dissolved in THF in a two-diameter recovery flask. After argon substitution, o-tolylmagnesium chloride (0.9M THF solution) (3.0 mL, 2.7 mmol) was slowly added under ice cooling, and the mixture was stirred at 60° C. for 1 hour. 2N hydrochloric acid was added until the reaction solution became acidic, the reaction solution was extracted with $CH_2Cl_2$. The organic layer was dried over anhydrous $Na_2SO_4$, and the solvent was removed under reduced pressure. A residue was roughly purified by column chromatography (silica gel, $CH_2Cl_2$/MeOH=100/0→80/20) and purified with HPLC (eluent, A/B=80/20→0/100, 20 minutes; A: $H_2O$ containing 0.1% TFA (v/v), B: MeCN/$H_2O$=80/20 containing 0.1% TFA (v/v)) to obtain Compound 6 (26.7 mg, yield 92%).

$^1$H-NMR (300 MHz, $CDCl_3$) δ 2.06 (s, 3H), 3.47 (s, 12H), 7.25 (d, 2H, J=9.5 Hz), 7.29 (m, 1H), 7.33 (d, 2H, J=9.5 Hz), 7.45-7.62 (m, 3H).

$^{13}$C-NMR (75 MHz, $CDCL_3$) δ 19.7, 44.4, 107.4, 117.4, 120.1, 127.3, 130.2, 130.3, 131.7, 132.0, 132.5, 137.5, 155.5, 159.0, 161.0.

HRMS (ESI$^+$): Calcd for [M]$^+$, 425.1187, Found, 425.1217 (+3.0 mmu).

Synthesis Example 2

(1) Synthesis of 2-(4-(dimethylamino)-2-hydroxybenzoyl)benzoic acid (Compound 7)

Compound 7

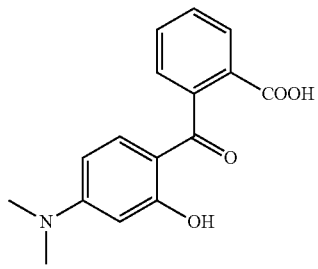

Compound 7 was synthesized according to Reference 2 (Sauers, R. R.; Husain, S. N.; Piechowski, A. P.; Bird, G. R. Dye. Pigment. 1987, 8 (1), 35-53).

(2) Synthesis of 2'-chloro-6'-(dimethylamino)-3-oxo-3H-spiro[isobenzofuran-1,9'-xanthene]-3'-yl trifluoromethanesulfonate (Compound 8)

Compound 8

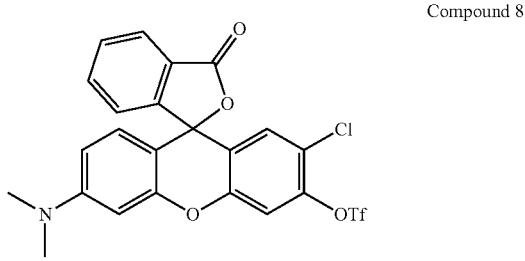 [SMILES: CN(C)c1ccc2c(c1)Oc1cc(OS(=O)(=O)C(F)(F)F)c(Cl)cc1C21OC(=O)c2ccccc21]

Compound 7 (863 mg, 3.0 mmol) and 4-chlororesorcinol (442 mg, 3.1 mmol) were dissolved in 85% phosphoric acid (5 mL), and the mixture was stirred at 170° C. for 3 hours.

After the reaction solution was cooled to room temperature, 60% HClO₄aq. (8 mL) was added, and the mixture was further stirred at 100° C. for 20 minutes. Ice water was added to the reaction solution, and then Kiriyama filtration was performed. The residue was dissolved in MeOH and then dried over anhydrous Na₂SO₄, and the solvent was removed under reduced pressure. A residue was dissolved in DMF (8 mL), N-phenylbis(trifluoromethanesulfonimide) (1.45 g, 4.1 mmol) and N,N-diisopropylethylamine (1.04 g, 8.1 mmol) were further added, and the mixture was stirred at room temperature under an argon atmosphere for 1 hour 40 minutes. Sat. NH₄Claq. was added to the reaction solution and extracted with a mixed solvent of AcOEt+hexane, the organic layer was dried over anhydrous Na₂SO₄, and the solvent was removed under reduced pressure. A residue was roughly purified by column chromatography (silica gel, CH₂Cl₂) to obtain a crudely purified product (1.12 g) of Compound 8.

(3) Synthesis of 2-ClTMR (Compound 9)

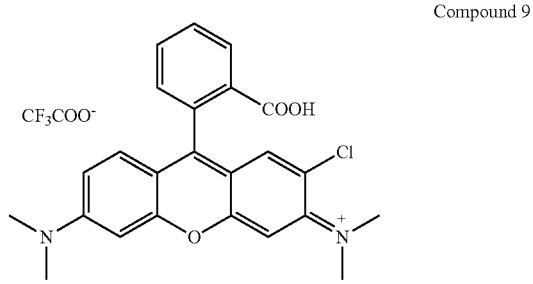

Compound 9

A crudely purified product (105 mg) of Compound 8, dimethylamine hydrochloride (164 mg, 2.01 mmol), and Cs₂CO₃ (1967 mg, 2.13 mmol) were dissolved in toluene (19 mL) in a Schlenk tube and replaced with argon. Then, Pd₂(dba)₃ (22 mg, 0.02 mmol) and xantphos (12 mg, 0.02 mmol) were added and replaced with argon again, and the mixture was stirred at 100° C. for 12 hours. The temperature of the reaction solution was returned to room temperature, and the reaction solution was filtered through Kiriyama. Then, the solvent was removed under reduced pressure. A residue was roughly purified by column chromatography (CH₂Cl₂/MeOH=95/5→0/100) and further purified with HPLC (eluent, A/B=80/20→0/100, 20 minutes; A: H₂O containing 0.1% TFA (v/v), B: MeCN/H₂O=80/20 containing 0.1% TFA (v/v)) to obtain Compound 9 (11 mg).

$^1$H-NMR (300 MHz, CD₂Cl₂) δ3.18 (s, 6H), 3.26 (s, 6H), 6.78 (s, 1H), 6.86 (dd, 1H, J=9.5 Hz, 3.0 Hz), 7.03 (s, 1H), 7.15 (d, 1H, J=9.5 Hz), 7.13 (s, 1H), 7.25-7.28 (m, 1H), 7.75-7.77 (m, 2H), 8.30-8.32 (m, 1H).

$^{13}$C-NMR (100 MHz, CD₃OD) δ 41.3, 43.7, 97.7, 105.2, 116.1, 116.6, 117.0, 124.2, 130.9, 131.8, 132.0, 132.0, 132.2, 132.5, 134.3, 136.0, 156.1, 158.1, 159.4, 159.8, 168.2.

HRMS (ESI⁺): Calcd for [M]⁺, 421.1319, Found, 421.1281 (−3.8 mmu).

Synthesis Example 3

(1) Synthesis of 2-MeTMR (Compound 10)

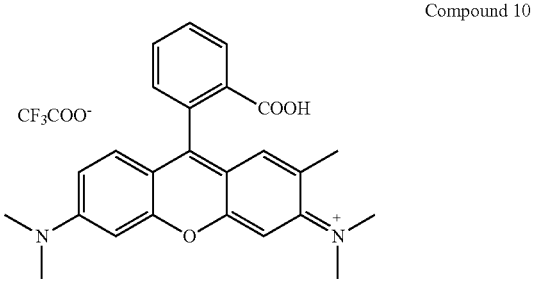

Compound 10

Compound 7 (299.2 mg, 1.05 mmol) and 3-dimethylamino-4-methylphenol (152.9 mg, 1.01 mmol) were added to 85% phosphoric acid (3 mL), and the mixture was stirred at 170° C. for 4 hours. After the reaction solution was cooled to room temperature, the solution was washed with H₂O using Sep-Pak (registered trademark) (Vac 35 cc (10 g) C18 Cartridges), and then eluted with MeOH. The solvent was removed under reduced pressure and purified by HPLC (eluent, A/B=70/30→0/100, 40 minutes; A: H₂O containing 0.1% TFA (v/v), B: MeCN/H₂O=80/20 containing 0.1% TFA (v/v)) to obtain Compound 9 (28.5 mg, yield 5%).

$^1$H-NMR (300 MHz, CD₂Cl₂) δ 2.30 (s, 3H), 3.13 (s, 6H), 3.24 (s, 6H), 6.77 (d, 1H, J=2.4 Hz), 6.84 (dd, 1H, J=9.5 Hz, J=2.7 Hz), 6.94 (s, 1H), 6.97 (s, 1H), 7.11 (d, 1H, J=9.3 Hz), 7.23-7.25 (m, 1H), 7.71-7.77 (m, 2H), 8.32-8.35 (m, 1H).

$^{13}$C-NMR (75 MHz, CD₃OD) δ 17.4, 30.7, 40.8, 94.8, 97.3, 114.7, 115.1, 115.3, 126.8, 130.1, 131.4, 131.5, 131.7, 132.3, 132.5, 133.9, 135.5, 158.4, 158.7, 159.3, 159.5, 161.2, 168.1.

HRMS (ESI⁺): Calcd for [M]⁺, 401.1865, Found, 401.1863 (−0.2 mmu).

Synthesis Example 4

(1) Synthesis of 6'-dimethylamino-2'-fluoro-3-oxo-3H-spiro(isobenzofuran-1,9'-xanthene)-3'-yl trifluoromethanesulfonate (Compound 11)

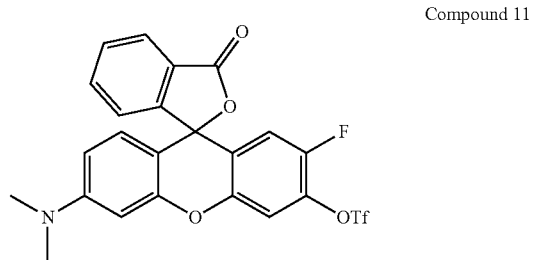 [SMILES: CN(C)c1ccc2c(c1)Oc1cc(OS(=O)(=O)C(F)(F)F)c(F)cc1C21OC(=O)c2ccccc21]

Compound 11

Compound 7 (288.7 mg, 1.0 mmol) and 4-fluororesorcinol (130.1 mg, 1.0 mmol) were dissolved in 85% phosphoric acid (3 mL), and the mixture was stirred at 170° C. for 4 hours. After the reaction solution was cooled to room temperature, 60% HClO₄aq. (3 mL) was added, and the mixture was further stirred at 100° C. for 25 minutes. Ice water was added to the reaction solution, and then Kiriyama filtration was performed. The residue was dissolved in MeOH and then dried over anhydrous $Na_2SO_4$, and the solvent was removed under reduced pressure. A residue was dissolved in DMF (5 mL), N-phenylbis(trifluoromethanesulfonimide) (548.1 mg, 1.5 mmol) and N,N-diisopropylethylamine (388.1 mg, 3.0 mmol) were further added, and the mixture was stirred at room temperature under an argon atmosphere for 3 hours. Sat. $NH_4Cl$aq. was added to the reaction solution and extracted with a mixed solvent of AcOEt and hexane, the organic layer was dried over anhydrous $Na_2SO_4$, and the solvent was removed under reduced pressure. A residue was purified by column chromatography (silica gel, $CH_2Cl_2$) to give Compound 11 (207.8 mg, yield 40%).

$^1$H-NMR (300 MHz, $CD_2Cl_2$) δ 2.98 (s, 6H), 6.47 (dd, 1H), 6.51 (d, 1H, J=2.2 Hz), 6.63 (d, 1H, J=8.8 Hz), 6.74 (d, 1H, J=10.3 Hz), 7.22 (m, 1H), 7.34 (d, 1H, J=6.6 Hz), 7.71 (m, 2H), 8.04 (m, 1H).

$^{13}$C-NMR (75 MHz, $CD_2Cl_2$) δ 40.3, 82.7, 98.4, 104.8, 110.0, 112.9, 116.4 (d, J=20.4 Hz), 119.1 (q, J=318.3 Hz), 121.6 (d, J=5.5 Hz), 124.3, 125.6, 127.0, 128.8, 130.7, 135.8, 137.8 (d, J=15.4 Hz), 148.4, 148.5, 149.7 (d, J=217.8 Hz), 152.5 152.7 (d, J=28.4 Hz), 169.1.

HRMS (ESI$^+$): Calcd for [M+H]$^-$, 510.0635, Found, 510.0626 (−0.9 mmu).

(2) Synthesis of 2-FTMR (Compound 12)

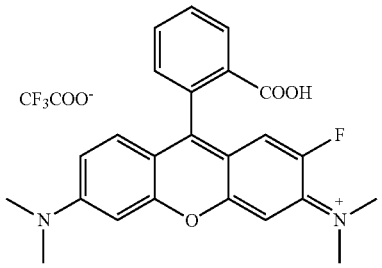

Compound 12

Compound 11 (102 mg, 0.20 mmol), dimethylamine hydrochloride (127 mg, 1.56 mmol), and $Cs_2CO_3$ (1137 mg, 3.49 mmol) were dissolved in toluene (15 mL) in a Schlenk tube and replaced with argon. Then, $Pd_2(dba)_3$ (103.5 mg, 0.11 mmol) and xantphos (58.4 mg, 0.10 mmol) were added and replaced with argon again, and the mixture was stirred at 100° C. for 17.5 hours. The temperature of the reaction solution was returned to room temperature, and the reaction solution was filtered through Kiriyama. Then, the solvent was removed under reduced pressure. A residue was purified by HPLC (eluent, A/B=70/30→0/100, 40 minutes; A: $H_2O$ containing 0.1% TFA (v/v), B: $MeCN/H_2O$=80/20 containing 0.1% TFA (v/v)) to obtain Compound 12 (11 mg, yield 11%).

$^1$H-NMR (300 MHz, $CD_3CN$) δ 3.15 (m, 12H), 0.6.70 (d, 1H, J=9.5 Hz), 6.73 (d, 1H, J=2.9 Hz), 6.80-6.86 (m, 2H), 6.94 (d, 1H, J=9.5 Hz), 7.26-7.29 (m, 1H), 7.72-7.78 (m, 2H), 8.17-8.20 (m, 1H).

$^{13}$C-NMR (75 MHz, $CD_3OD$) δ 41.1, 43.3 (d, J=8.1 Hz), 97.3, 101.8 (d, J=5.0 Hz), 114.6, 114.7, 114.9, 115.2, 115.8, 116.5, 131.3, 131.7, 132.1 (d, J=8.1 Hz), 132.6, 134.0, 135.0, 150.0, (d, J=11.2 Hz), 152.1 (d, J=250.5 Hz), 155.6, 159.4, (d, J=3.1 Hz), 161.3, 168.0.

HRMS (ESI$^+$): Calcd for [M]$^+$, 405.1615, Found, 405.1590 (−2.5 mmu).

Synthesis Example 4

(1) Synthesis of 2-Cl triMe rhodamine (Compound 13)

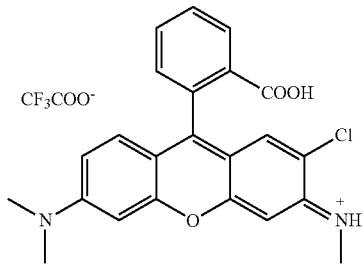

Compound 13

A crudely purified product (108.2 mg) of Compound 8, methylamine hydrochloride (140 mg, 2.08 mmol), and $Cs_2CO_3$ (2062 mg, 6.33 mmol) were dissolved in toluene (18 mL) in a Schlenk tube and replaced with argon. Then, $Pd_2(dba)_3$ (19.5 mg, 0.02 mmol) and xantphos (13.5 mg, 0.02 mmol) were added and replaced with argon again, and the mixture was stirred at 100° C. overnight. The temperature of the reaction solution was returned to room temperature, and the reaction solution was filtered through Kiriyama. Then, the solvent was removed under reduced pressure. A residue was roughly purified by column chromatography ($CH_2Cl_2$/MeOH=95/5) and further purified with HPLC (eluent, A/B=70/30→0/100, 25 minutes; A: $H_2O$ containing 0.1% TFA (v/v), B: $MeCN/H_2O$=80/20 containing 0.1% TFA (v/v)) to obtain Compound 13 (16 mg).

Synthesis Example 5

(1) Synthesis of 3,6-bis(N,N-dimethylamino)Si-xanthone (Compound 14)

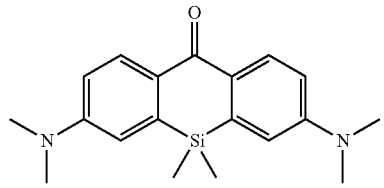

Compound 14

Compound 14 was synthesized according to Reference 3 (Lukinavicius, G.; Umezawa, K.; Olivier, N.; Honigmann, A.; Yang, G.; Plass, T.; Mueller, V.; Reymond, L.; Correa, I. R.; Luo, Z. G.; Schultz, C.; Lemke, E. A.; Heppenstall, P.; Eggeling, C.; Manley, S.; Johnsson, K. Nat. Chem. 2013, 5 (2), 132-139).

(2) Synthesis of SiR650 (Compound 1b)

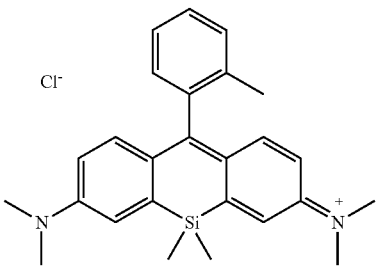

Compound 15

Compound 15 (61.1 mg, 0.19 mmol) was dissolved in THF in a two-diameter recovery flask. After argon substitution, o-tolylmagnesium chloride (1.0M THF solution) (9.5 mL, 9.5 mmol) was slowly added under ice cooling, and the mixture was stirred at 60° C. for 60 minutes. 2N hydrochloric acid was added until the reaction solution became acidic, the reaction solution was extracted with $CH_2Cl_2$. The organic layer was washed with $H_2O$, dried over anhydrous $Na_2SO_4$, and then removed under reduced pressure. A residue was purified by column chromatography (silica gel, $CH_2Cl_2$/MeOH=93/7-85/15) to give Compound 15 (75.4 mg, yield 91%).

$^1$H-NMR (300 MHz, $CDCl_3$) δ 0.63 (s, 3H), 0.65 (s, 3H), 2.03 (s, 3H), 3.42 (s, 12H), 6.64 (dd, 2H, J=9.5 Hz, 2.9 Hz), 7.06-7.09 (m, 3H), 7.21 (d, J=2.9 Hz, 2H), 7.31-7.35 (m, 2H), 7.42-7.44 (m, 1H).

$^{13}$C-NMR (75 MHz, $CDCl_3$) δ −0.3, 0.0, 20.0, 41.8, 114.6, 121.4, 126.2, 128.2, 129.5, 130.9, 136.2, 139.0, 142.1, 149.1, 154.7, 170.5.

HRMS (ESI$^+$): Calcd for [M]$^+$, 399.2257, Found, 399.2266 (+0.9 mmu).

(3) Synthesis of 4-Cl TMSiR (Compound 16)

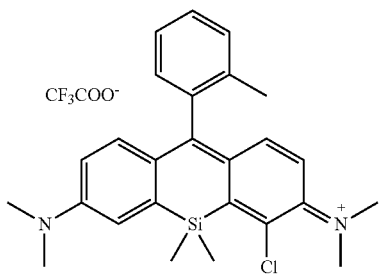

Compound 16

Compound 14 (80.9 mg, 0.19 mmol) was dissolved in MeOH (10 mL), and a 1.5M NaOCl solution (280 μL, 0.42 mmol) dissolved in 4 mL 0.1N NaOHaq. was added under ice cooling with stirring. The resulting solution was stirred at room temperature for 30 minutes, and MeOH was removed from the reaction solution under reduced pressure. Then, 2N hydrochloric acid was added, and the mixture was extracted with $CH_2Cl_2$. The organic layer was dried over anhydrous $Na_2SO_4$, and the solvent was removed under reduced pressure. A residue was purified by HPLC (eluent, A/B=70/30→0/100, 40 minutes; A: $H_2O$ containing 0.1% TFA (v/v), B: MeCN/$H_2O$=80/20 containing 0.1% TFA (v/v)) to obtain Compound 16 (5.4 mg, yield 5%).

$^1$H-NMR (400 MHz, $CD_2Cl_2$): δ 0.74 (s, 3H), 0.75 (s, 3H), 2.00 (s, 3H), 3.13 (s, 6H), 3.48 (br s, 6H), 6.92 (dd, J=10.1, 2.7 Hz, 1H), 6.96 (d, J=9.1 Hz, 1H), 7.05 (d, J=9.1 Hz, 1H), 7.11 (d, J=7.3 Hz, 1H), 7.14 (d, J=10.1 Hz, 1H), 7.32-7.43 (m, 2H), 7.46 (d, J=7.3 Hz, 1H), 7.48 (d, J=2.3 Hz, 1H).

HRMS (ESI+): Calcd for [M]+, 433.1867; found, 433.1867 (+0.0 mmu).

The HPLC chromatogram after purification is shown below. (A/B=70/30→0/100, 40 min; A: $H_2O$ containing 0.1% TFA (v/v), B: MeCN/$H_2O$=80/20 containing 0.1% TFA (v/v). 1.0 mL/min flow rate. Detection at 650 nm).

Synthesis Example 6

(1) Synthesis of 4,5-diCl-3,6-bis(N,N-dimethylamino)Si-xanthone (Compound 17)

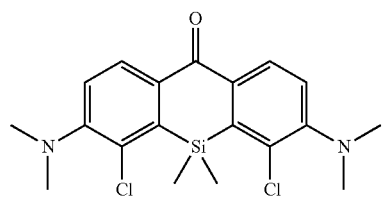

Compound 17

Compound 14 (333 mg, 1.02 mmol) was dissolved in MeOH (90 mL), and a 1.5M NaOCl solution (4.0 mL, 6.00 mmol) dissolved in 6 mL 0.1N NaOHaq. was added under ice cooling with stirring. The resulting solution was stirred at room temperature for 1.5 hours, and MeOH was removed from the reaction solution under reduced pressure. Then, sat. NaHCO$_3$aq. was added, and the mixture was extracted with $CH_2Cl_2$. The organic layer was dried over anhydrous $Na_2SO_4$, and the solvent was removed under reduced pressure. A residue was purified by column chromatography (silica gel, $CH_2Cl_2$) to give Compound 17 (224.1 mg, yield 56%).

$^1$H-NMR (400 MHz, $CD_2Cl_2$): δ 0.79 (s, 6H), 2.89 (s, 12H), 7.20 (d, J=8.7 Hz, 2H), 8.31 (d, J=8.7 Hz, 2H)

$^{13}$C-NMR (100 MHz, $CD_2Cl_2$): δ-1.3, 43.2, 121.0. 129.7, 132.4, 134.6, 140.6, 153.9, 184.7.

HRMS (ESI$^+$): Calcd for [M+H]$^+$, 393.0957; found, 393.0954 (−0.3 mmu).

(2) Synthesis of 4,5-diCl TMSiR (Compound 18)

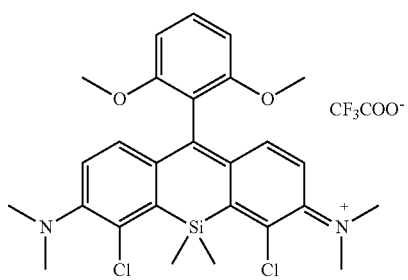

Compound 18

2-Bromo-1,3-dimethoxybenzene (599.6 mg, 2.76 mmol) was dissolved in THF (10 mL) under Ar substitution, sec-BuLi (1.0M hexane solution) (2.70 mL, 2.70 mmol) was added at −78° C., and the mixture was stirred for 30 minutes. Compound 17 (108.6 mg, 0.28 mmol) dissolved in THF (5 mL) was added thereto, and the mixture was stirred at room temperature for 2 hours. 2N hydrochloric acid was added thereto to terminate the reaction. The reaction solution was extracted with $CH_2Cl_2$, the organic layer was dried over anhydrous $Na_2SO_4$, and the solvent was removed under reduced pressure. A residue was purified by column chromatography (silica gel, $CH_2Cl_2$/MeOH=95/5 to 85/15) and further purified with HPLC (eluent, A/B=70/30→0/100, 40 minutes; A: $H_2O$ containing 0.1% TFA (v/v), B: MeCN/$H_2O$=80/20 containing 0.1% TFA (v/v)) to obtain Compound 18 (19.3 mg, yield 11%).

$^1$H-NMR (400 MHz, $CD_2Cl_2$): δ 0.91 (s, 6H), 3.31 (s, 12H), 3.63 (s, 6H), 6.71 (d, J=8.2 Hz, 2H), 6.79 (d, J=9.6 Hz, 2H), 7.25 (d, J=9.1 Hz, 2H), 7.50 (t, J=8.5 Hz, 1H)

$^{13}$C-NMR (100 MHz, $CD_2Cl_2$): δ −2.1, 44.5, 56.4, 104.4, 115.9, 119.3, 131.2, 131.8, 132.0, 140.4, 148.7, 156.9, 157.7, 170.0.

HRMS (ESI$^+$): Calcd for [M]$^+$, 513.1532; found, 513.1533 (+0.1 mmu).

Synthesis Example 7

(1) Synthesis of 5'-chloro-3'-dimethylamino-3-oxo-3H-spiro(isobenzofuran-1,9'-xanthene)-6'-yl trifluoromethanesulfonate (Compound 19)

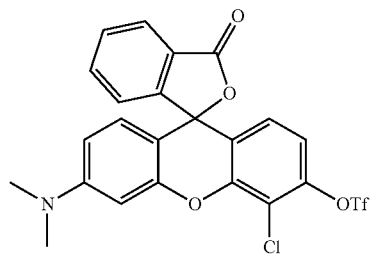

Compound 19

Compound 7 (574 mg, 2.0 mmol) and 2-chlororesorcinol (287 mg, 2.0 mmol) were dissolved in 85% phosphoric acid (4 mL), and the mixture was stirred at 170° C. for 3 hours. After the reaction solution was cooled to room temperature, 60% $HClO_4$aq. (5.0 mL) was added, and the mixture was further stirred at 100° C. for 20 minutes. Ice water was added to the reaction solution, and then Kiriyama filtration was performed. The residue was dissolved in MeOH and then dried over anhydrous $Na_2SO_4$, and the solvent was removed under reduced pressure. A dried residue was dissolved in DMF (8.0 mL), N-phenylbis(trifluoromethanesulfonimide) (1264 mg, 3.5 mmol) and N,N-diisopropylethylamine (890 mg, 6.8 mmol) were further added, and the mixture was stirred at room temperature under an argon atmosphere for 14 hours. Sat. $NH_4Cl$aq. was added to the reaction solution and extracted with a mixed solvent of AcOEt and hexane, the organic layer was dried over anhydrous $Na_2SO_4$, and the solvent was removed under reduced pressure. A residue was purified by column chromatography (silica gel, $CH_2Cl_2$) to give Compound 19 (990 mg, yield 95%).

$^1$H-NMR (400 MHz, $CD_2Cl_2$) δ 3.89 (s, 6H), 6.38 (dd, 1H, J=8.8 Hz, 2.4 Hz), 6.50-6.54 (m, 2H), 6.71 (d, 1H, J=8.8 Hz), 6.94 (d, 1H, J=8.8 Hz), 7.07-7.10 (m, 1H), 7.56-7.61 (m, 2H) 7.90-7.92 (m, 1H).

$^{13}$C-NMR (100 MHz, $CD_2Cl_2$) δ 40.4, 82.7, 98.7, 105.3, 110.3, 116.6, 117.1, 119.0, (q, J=322 Hz), 122.0, 124.3, 125.5, 127.1, 127.6, 128.8, 130.6, 135.7, 147.0, 149.6, 152.3, 152.7, 153.0, 169.2.

HRMS (ESI$^+$): Calcd for [M+H]$^-$, 526.0339, Found, 526.0307 (−3.2 mmu).

(2) Synthesis of 2'-COOH-4-Cl TMR (Compound 20)

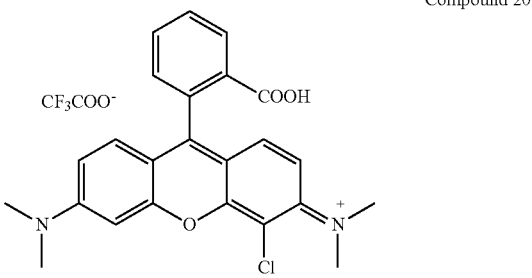

Compound 20

Compound 19 (105 mg, 0.20 mmol), dimethylamine hydrochloride (163 mg, 2.00 mmol), and $Cs_2CO_3$ (2092 mg, 6.42 mmol) were dissolved in toluene (15 mL) in a Schlenk tube and replaced with argon. Then, $Pd_2(dba)_3$ (22 mg, 0.02 mmol) and xantphos (13 mg, 0.02 mmol) were added and replaced with argon again, and the mixture was stirred at 100° C. for 12 hours. The temperature of the reaction solution was returned to room temperature, and the reaction solution was filtered through Kiriyama. Then, the solvent was removed under reduced pressure. 2N hydrochloric acid was added to the residue, and the mixture was extracted with $CH_2Cl_2$. The organic layer was washed with $H_2O$ and dried over anhydrous $Na_2SO_4$, and the solvent was removed under reduced pressure. A residue was purified by HPLC (eluent, A/B=70/30→0/100, 25 minutes; A: $H_2O$ containing 0.1% TFA (v/v), B: MeCN/$H_2O$=80/20 containing 0.1% TFA (v/v)) to obtain Compound 9 (8 mg, yield 7%).

$^1$H-NMR (300 MHz, $CD_2Cl_2$) δ 3.11 (s, 6H), 3.20 (s, 6H), 6.76 (dd, 1H, J=8.8 Hz, 2.9 Hz), 6.82 (d, 1H, J=2.9 Hz), 6.87-6.94 (m, 2H), 6.97 (d, 1H, J=9.5 Hz), 7.20-7.23 (m, 1H), 7.68-7.76 (m, 2H), 8.20-8.23 (m, 1H).

$^{13}$C-NMR (100 MHz, $CD_3OD$) δ 41.2, 43.8, 98.1, 109.7, 114.8, 116.2, 116.8, 118.0, 129.0, 130.3, 131.4, 131.6, 132.1, 134.4, 153.5, 157.4, 158.6, 159.1, 168.6.

HRMS (ESI$^+$): Calcd for [M]$^+$, 421.1319, Found, 421.1290 (−2.9 mmu).

Example 1

The optical properties of the compound synthesized in the above Synthesis Examples were evaluated. The results are illustrated in FIG. 4.

(a to c) of FIG. 4 illustrate chemical structures of tetramethylrhodamine (TMR) (a), 4-Cl TMR (b) and 4,5-diCl TMR (c), the fluorescence quantum yields ($\Phi_{fl}$) in MeOH containing 0.1% TFA, absorption maximum ($\lambda_{abs}$) and emission maximum ($\lambda_{em}$). $\Phi_{fl}$ is a relative fluorescence quantum yield determined with reference to Rhodamine B ($\Phi_{fl}$=0.65) of EtOH.

(d to f) of FIG. 4 illustrates absorption spectra and emission spectra of 1 μM TMR (d), 4-Cl TMR (e) and 4,5-diCl TMR (f) in MeOH containing 0.1% TFA and 0.1% DMSO.

The three kinds of synthesized compounds all showed similar absorption spectra. On the other hand, while TMR showed strong fluorescence with $\Phi_{fl}$=0.399, 4-Cl TMR and 4,5-diCl TMR in which the Cl group was substituted at the ortho position of the dimethylamino group had fluorescence quantum yields of 0.003 and 0.001, respectively, and it was found that almost non-fluorescence was exhibited. From this result, it became clear that as expected from the study by the computational chemistry, a strongly fluorescent rhodamine dye could be made non-fluorescent by introducing a bulky substituent at the ortho position of the xanthene cyclic dimethylamino group.

Example 2

Next, in order to examine whether the non-fluorescence of the newly developed non-fluorescent rhodamine was due to the production of the TICT state, solvent viscosity dependence of the fluorescence quantum yield was examined. Specifically, the absorption, fluorescence spectrum and fluorescence quantum yield were measured in three types of solvents including MeOH ($\varepsilon_r$=32.6, η=0.61 cP), ethylene glycol ($\varepsilon_r$=38.7, η=19.9 cP) and glycerol ($\varepsilon_r$=42.5, η=1412 cP). Since these three solvents have similar dielectric constants $\varepsilon_r$, but significantly different viscosities n, it is possible to examine the viscosity dependence of the optical properties of the compound. It was expected that if the formation of the TICT state was promoted by the steric hindrance due to the introduction of the substituent, while quenching was performed by the formation of the TICT state in MeOH, in a highly viscous solvent such as glycerol, a rate of intramolecular twist became slow, and the transition to the TICT state was suppressed, so that the fluorescence quantum yield would increase.

FIG. 5 actually illustrates the solvent viscosity dependence of the optical properties of 4-Cl TMR.

(a) of FIG. 5 is $\Phi_{fl}$ of 4-Cl TMR in glycerol, ethylene glycol and MeOH. $\Phi_{fl}$ is a relative fluorescence quantum yield determined with reference to Rhodamine B ($\Phi_{fl}$=0.65) of EtOH. (b and c) of FIG. 5 illustrate the absorption spectrum (b) and the emission spectrum (c) of 1 μM 4-Cl TMR in glycerol, ethylene glycol and MeOH.

As a result of the experiment, while 4-Cl TMR was quenched with $\Phi_{fl}$=0.003 in MeOH with low viscosity, in ethylene glycol and glycerol with high viscosity, on were 0.01 and 0.09, respectively, and the increase in fluorescence quantum yield was observed. Therefore, the newly developed non-fluorescent rhodamine had the property that the fluorescence intensity increased according to the solvent viscosity, which supported that the quenching was actually performed by the TICT mechanism.

Example 3

Next, in order to confirm that the quenching of the newly developed non-fluorescent rhodamines was caused by steric hindrance, derivatives with different degrees of steric hindrance were synthesized, and their optical properties were evaluated. Here, the present examination was performed using a derivative where a substituent at the 2' position of the benzene ring directly bonded to the xanthene ring was changed from a Me group to a COOH group, and, in addition, a substitution position of a substituent causing steric hindrance was changed from the 4-position to the 2-position of the xanthene ring.

First, the optical properties of a compound in which the Cl group was introduced at the 2-position of the xanthene ring were obtained. As a result, since 2-Cl TMR also exhibited non-fluorescence like 4-Cl TMR, it became clear that in the Cl group which was a substituent causing steric hindrance, quenching due to the formation of the TICT state occurred even in a case of substitution at the 2-position of the xanthene ring.

Next, it was decided to synthesize a derivative in which the substituent at the 2-position on the xanthene ring was changed to a substituent other than the Cl group, and to investigate its optical properties. Specifically, referring to the Taft steric factor (Reference 4: Toshio Fujita. Synthetic Organic Chemistry 1978, 36 (10), 832-833) known as a parameter indicating a three-dimensional size of a substituent, a derivative where the Me group having a three-dimensional size equivalent to that of the Cl group and the F group sterically smaller than the Cl group and the Me group were substituted at the 2-position of the xanthene ring was synthesized, and whether the fluorescence quantum yield changed depending on the size of the substituent was examined. As a result, the fluorescence quantum yield was about 1% in 2-Me TMR substituted with a $CH_3$ group having a steric size equivalent to that of the Cl group, and almost non-fluorescence was exhibited. On the other hand, the fluorescence quantum yield was about 10% in 2-F TMR substituted with a F group, which was considered to further alleviate the effect of steric hindrance, and the fluorescence was exhibited. From this result, it was strongly suggested that the quenching of the newly developed non-fluorescent rhodamine was caused by steric hindrance between the dimethylamino group on the xanthene ring and the substituent on the ortho position.

(a to c) of FIG. 6 illustrate chemical structures of 2-Cl TMR (a), 2-Me TMR (b) and 2-F TMR (c), the fluorescence quantum yields (Oni) in MeOH containing 0.1% TFA, absorption maximum ($\lambda_{abs}$) and emission maximum ($\lambda_{em}$). $\Phi_{fl}$ is a relative fluorescence quantum yield determined with reference to Rhodamine B ($\Phi_{fl}$=0.65) of EtOH.

(d to f) of FIG. 6 illustrates the absorption spectra and the emission spectra of 1 μM 2-Cl TMR (a), 2-Me TMR (b) and 2-F TMR (c) in MeOH containing 0.1% TFA and 0.1% DMSO.

Example 4

Next, a compound in which the substituent on the amino group was changed from a dimethyl group to a monomethyl group was synthesized, and its optical properties were evaluated. In this compound, since it is considered that steric hindrance between the alkyl group on the amino group and the substituent on the ortho position, which causes quenching, is relieved, it has been expected that the fluorescence may be recovered. The results are illustrated in FIG. 7.

(a) of FIG. 7 illustrates $\Phi_{fl}$, $\lambda_{abs}$ and $\lambda_{em}$ of 2-Cl triMe rhodamine in MeOH containing 0.1% TFA. (b) of FIG. 7 illustrates the absorption spectrum and the emission spectrum of 1 μM 2-Cl triMe rhodamine in MeOH containing 0.1% TFA.

The developed compound exhibited fluorescence with a fluorescence quantum yield of 15%, and it became clear that when by actually using a substituent on the amino group as a monomethyl group, the steric hindrance was relieved, and the fluorescence was recovered.

From the above results, making rhodamine non-fluorescent by structural modification different from conventional molecular design was successfully made by performing logical molecular design based on computational chemistry. Next, application examples that are considered to be possible by using these novel non-fluorescent rhodamines are shown.

Application Example: Application as Novel Fluorescence Quenching Group

It is considered that a novel fluorescence quenching group (dark quencher) can be developed by applying the non-fluorescent rhodamines of the present invention. A fluorescence quenching group is a compound that is deactivated by a process other than fluorescence after being excited by light, and is typically used as an acceptor of FRET, for example. Among the existing fluorescence quenching groups, typical examples that are commercially available include Dabcyl, Black Hole Quencher (BHQ), and QSY series.

Dabcyl is a fluorescence quenching group that is considered to become non-fluorescent by an azo structure included in the molecule, and dabcyl is considered to be highly versatile because of its simple structure as illustrated in FIG. 8. However, the wavelength that can be quenched is a slightly short wavelength of 500 nm or less (Reference 5: Johansson, M. K. Methods Mol. Biol. 2006, 335, 17-29).

Black Hole Quencher (BHQ) series (Reference 6: M. Cook, R.; Lyttle, M.; Dick, D., U.S. Pat. No. 7,019,129, 2006) is also a quenching group that is considered to become non-fluorescent by the azo structure in the molecule and can quench fluorescence with a longer wavelength compared to dabcyl. In these quenchers having the azo structure, although there is a quenching group corresponding to a wide wavelength band (FIG. 9), the azo structure is a structure that is easily reduced, and may be unstable in vivo or in cells.

QSY series (Reference 7: The Molecular Probes Handbook) are quenching groups capable of quenching fluorescence having a longer wavelength than that of Dabcyl, and QSY7, QSY9, and QSY21 are diarylrhodamines in which an aryl group is bonded to N atom on the xanthene ring of rhodamine (FIG. 10).

Since the novel quenching group of the present invention does not have an azo structure, it is considered that the quenching group is more stable even in a reduced state than Dabcyl or BHQ.

A difference between the QSY series and the present quenching group is a difference between quenching by introducing an aryl group into N atom and quenching by introducing a substituent such as a Cl group or a Me group at the ortho position. Examples of advantages brought about by this difference may include the following.

Since introduction of a highly lipophilic aryl group is not required in the quenching, water solubility increases, and handling is expected to be improved.

Since the molecular size is more compact than the QSY series, enzyme recognition is expected to be improved when the quenching group is used as an acceptor for FRET or the like.

Thus, the newly developed non-fluorescent rhodamine is expected to be a more practical fluorescence quenching group than the existing fluorescence quenching groups.

Example 5

Development of Near-Infrared Fluorescence Quenching Group Based on TICT Mechanism In developing a fluorescence quenching group that applies new non-fluorescent rhodamines, it is desirable to be able to develop a fluorescence quenching group that can be used in a wide wavelength band. Rhodamines are known to show various absorption wavelengths by substituting the O atom at the 10-position of the xanthene ring to a Si atom, a C atom, a Ge atom, a P atom, and $SO_2$, and if other 10-position substituted rhodamines can also be made non-fluorescent by the molecular design of the present invention, it is considered that a fluorescence quenching group over various wavelengths can be developed. Thus, the present inventors have examined whether Si-rhodamine (SiR)s having a Si atom substituted at the 10-position of the xanthene ring, which are examples of these 10-position substituted rhodamines, can be made non-fluorescent by the present molecular design. SiR is known to have a wavelength of about 90 nm longer than that of O-rhodamine, and is a rhodamine that has excellent in tissue permeability and exhibits absorbance in a near infrared region with little phototoxicity.

Specifically, a compound having a Cl group substituted at the 4-position on the xanthene ring of SiR and a compound having a Cl group substituted at the 4,5-positions were synthesized, and their optical properties were measured. In 4,5-diCl TMSiR, the OMe group was substituted at the 2' and 6'-positions of the benzene ring in order to prevent nucleophilic attack at the 9-position between xanthenes by the nucleophile.

(a and b) of FIG. 11 illustrate chemical structures of (a) 4-Cl TMSiR and (b) 4,5-diCl TMSiR. (c and d) of FIG. 11 illustrate normalized absorption spectrum (solid line) and emission spectrum (broken line) of 4-Cl TMSiR (c) and 4,5-diCl TMSiR (d).

The fluorescence quantum yield of 4-Cl TMSiR was 1%, the fluorescence quantum yield of 4,5-diCl TMSiR was 0.1% or less, and both compounds exhibited almost non-fluorescence. From this result, it became clear that the quenching by the present molecular design can be applied to SiRs, and it was shown that a novel fluorescence quenching group having various wavelengths can be developed.

Example 6

Development of Novel Fluorescent Probe Capable of Detecting N-Dealkylation Activity of P450 (1)

Utilizing the novel non-fluorescent rhodamines of the present invention, it is possible to develop a new fluorescent probe capable of detecting the N-dealkylation reaction of P450.

Although P450 is a metabolic enzyme responsible for the redox reaction in a phase I reaction of drug metabolism, inhibitory and induction of P450 by drugs cause drug-drug interactions, so that it is important to measure the P450 inhibitory and the inducing activity of drug candidate compounds at the early stage of the drug discovery process. In order to rapidly examine multiple samples, it is necessary to measure the inhibitory action and inducing action of drug candidate compounds on P450 with high throughput, and as such a method, a fluorescence method for measuring P450 activity by fluorescence is used.

Although fluorescent probes that recover fluorescence by being metabolized to P450 have already been developed, many fluorescent probes have poor P450 subtype selectivity and can only be used for P450 activity evaluation with purified enzymes (Reference 8: Jurica, J.; Sulcova, A. In Vivo (Brooklyn). 2011). Furthermore, many of the fluorescent probes are often not suitable for application in living cells or individual animals because of their short wavelength and low water solubility.

Therefore, if a new rhodamine-based P450 enzyme-activity-detecting fluorescent probe can be developed, this fluorescent probe can be used as a P450 activity-detecting fluorescent probe having excellent properties such as long wavelength, high water solubility, and high photobleaching resistance.

FIG. 12 illustrates a specific design. In the newly developed non-fluorescent rhodamine, the steric hindrance of the alkyl group on N atom and the substituent on the ortho position is the cause of non-fluorescence, as described above. Therefore, it is considered that the alkyl group on the amino group is removed due to the N-dealkylation activity of P450 to relieve the steric hindrance and restore the fluorescence.

While most of the existing P450 activity detection probes use the O-dealkylation reaction as a fluorescence OFF/ON switch, in the novel fluorescent probe examined this time and using N-dealkylation as a switch, it is possible that reactivity and subtype selectivity different from those of the existing probes will be exhibited.

In fact, as an initial examination, it was examined whether the fluorescence increase was observed by metabolizing the newly developed non-fluorescent rhodamines by P450. The results are illustrated in FIG. 13.

FIG. 13 illustrates time-dependent fluorescence changes of a NADPH producing system ($MgCl_2$: 1.5 mM, glucose-6-phosphate: 3 mM, $NADP^+$: 0.3 mM, glucose-6-phosphate dehydrogenase: 0.5 U/mL) and 1 µM rhodamine derivative using 11 types of P450 subtypes in 0.1M potassium phosphate buffer (pH 7.4) (Ex.544 nm/Em.590 nm).

The developed non-fluorescent rhodamines were metabolized to several P450 subtypes and showed the increase in fluorescence. In particular, it became clear that these non-fluorescent rhodamines showed the increase in fluorescence upon being recognized by several P450 subtypes, and among them, they tended to be well recognized by CYP3A4. CYP3A4 is the subtype most contributing to the oxidation reaction by CYP, and accounts for most of CYPs existing in the liver. Since CYP3A4 is a metabolic enzyme involved in the metabolism of many drugs, a fluorescent probe that detects enzymatic activity of CYP3A4 by fluorescence in cells or individual animals can be a useful tool for predicting drug-drug interactions in drug discovery.

Synthesis Example 8

(1) Synthesis of Compound 21

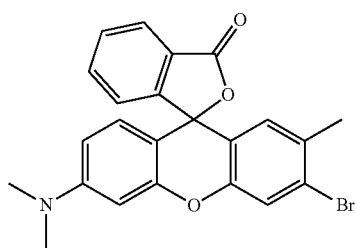

Compound 21

Compound 7 (1.15 g, 4.02 mmol) and 3-bromo-4-methylphenol (1.02 g, 5.46 mmol) were dissolved in methanesulfonic acid (6 mL), and the mixture was stirred at 100° C. for 1 hour. The reaction solution was neutralized with a 10N aqueous NaOH solution and extracted with $CH_2Cl_2$. The organic layer was dried over anhydrous $Na_2SO_4$, and the solvent was removed under reduced pressure. A residue was washed with MeOH to obtain a compound. (1.56 g)

$^1$H-NMR (400 MHz, $CD_2Cl_2$): δ 2.20 (s, 3H), 2.95 (s, 6H), 6.39 (dd, J=8.8 Hz, 2.9 Hz, 1H), 6.45 (d, J=2.2 Hz, 1H), 6.58-6.61 (m, 2H), 7.13-7.16 (m, 1H), 7.46 (s, 1H), 7.60-7.66 (m, 2H), 8.01-8.04 (m, 1H).

$^{13}$C-NMR (100 MHz, $CD_2Cl_2$): δ 22.0, 40.1, 83.2, 98.3, 105.5, 108.9, 118.4, 120.5, 123.8, 124.9, 126.0, 126.6, 128.5, 129.0, 129.6, 132.7, 134.9, 149.9, 152.0, 152.1, 153.1, 169.5.

HRMS (ESI+): Calcd for $[M]^+$, 436.0548; found, 436.0589 (+4.1 mmu).

(2) Synthesis of Compound 22

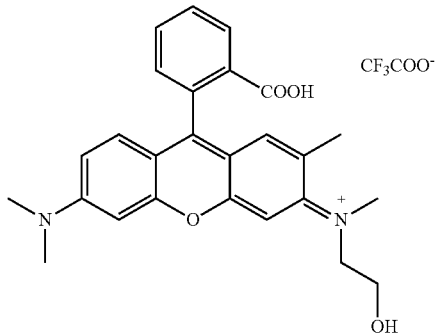

Compound 22

Compound 21 (444 mg, 1.02 mmol), 2-(methylamino)methanol (799 µL, 10.0 mmol), $Cs_2CO_3$ (1650 mg, 5.06 mmol), $Pd_2(dba)_3$ (45.5 mg, 0.05 mmol), and xantphos (87.7 mg, 0.15 mmol) were added to toluene (20 mL) and replaced with argon, and the mixture was stirred at 100° C. for 20 hours. The reaction solution was returned to room temperature, water was added, and the mixture was extracted with $CH_2Cl_2$. The organic layer was dried over anhydrous $Na_2SO_4$, and the solvent was removed under reduced pressure. A residue was purified with reverse phase medium pressure fractionation (eluent, A/B=90/10→0/100; A: $H_2O$ containing 0.1% TFA (v/v), B: MeCN containing 0.1% TFA (v/v)) to obtain Compound 22 (138 mg, yield 25%).

$^1$H-NMR (400 MHz, $CD_3OD$) δ 8.32-8.34 (m, 1H), 7.77-7.86 (m, 2H), 7.38-7.40 (m, 1H), 7.23 (s, 1H), 7.17 (d, J=9.6 Hz, 1H), 7.11 (dd, J=9.6, 2.3 Hz, 1H), 7.01 (d, J=2.3 Hz, 1H), 6.96 (d, J=0.9 Hz, 1H), 3.81 (t, J=5.7 Hz, 2H), 3.62 (t, J=5.5 Hz, 2H), 3.32 (s, 6H), 3.21 (s, 3H), 2.33 (s, 3H); $^{13}$C NMR (100 MHz, $CD_2Cl_2$): d 18.1, 40.4, 41.8, 57.8, 59.4, 98.5, 106.6, 108.4, 109.2, 114.1, 124.3, 125.1, 127.5, 128.8, 129.0, 129.9, 130.2, 135.1, 150.9, 152.7, 153.0, 153.3, 154.7, 169.7; HRMS ($ESI^+$): Calcd for $[M]^+$, 431.1971; found, 431.1978 (+0.7 mmu).

Synthesis Example 9

Synthesis of Compound 23

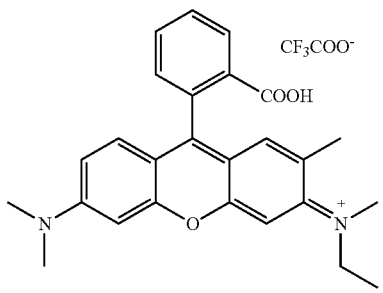

Compound 23

Compound 21 (59.6 mg, 0.147 mmol), N-ethylmethylamine (214 µL, 25.1 mmol), $Cs_2CO_3$ (202 mg, 0.620 mmol), $Pd_2(dba)_3$ (10.9 mg, 0.0119 mmol), and xantphos (10.3 mg, 0.0178 mmol) were added to toluene (5 mL), and the mixture was stirred at 110° C. for 3 hours and then stirred at 130° C. for 1 hour using a microwave synthesizer (Monowave 300 manufactured by Anton Paar Gmbh). The reaction solution was returned to room temperature, water was added, and the mixture was extracted with $CH_2Cl_2$. The organic layer was dried over anhydrous $Na_2SO_4$, and the solvent was removed under reduced pressure. A residue was purified by HPLC (eluent, A/B=70/30→0/100; A: $H_2O$ containing 0.1% TFA (v/v), B: $MeCN/H_2O$=80/20 containing 0.1% TFA (v/v)) to obtain Compound 23 (9.6 mg, 0.018 mmol, yield 12%).

$^1$H-NMR (400 MHz, $CD_3OD$) δ 8.33 (d, J=7.8 Hz, 1H), 7.82 (dtd, J=20.2, 7.5, 1.3 Hz, 2H), 7.39 (d, J=7.3 Hz, 1H), 7.17-7.19 (m, 2H), 7.11 (dd, J=9.6, 2.3 Hz, 1H), 7.01 (d, J=2.7 Hz, 1H), 6.97 (s, 1H), 3.49 (q, J=7.2 Hz, 2H), 3.32 (s, 6H), 3.14 (s, 3H), 2.31 (s, 3H), 1.29 (t, J=7.1 Hz, 3H); HRMS (ESI$^+$): Calcd for [M]$^+$, 415.2022; found, 415.2041 (+1.89 mmu).

The HPLC chromatogram after purification is shown below. (A/B=80/20→0/100, 25 min; A: $H_2O$ containing 0.1% TFA (v/v), B: $MeCN/H_2O$=80/20 containing 0.1% TFA (v/v). 1.0 mL/min flow rate. Detection at 560 nm).

Synthesis Example 10

Synthesis of Compound 24

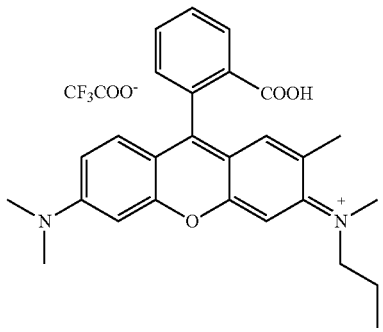

Compound 24

Compound 21 (108 mg, 0.248 mmol), N-methylpropylamine (500 µL, 4.97 mmol), $Cs_2CO_3$ (429 mg, 1.32 mmol), and RuPhos Pd G3 (41.8 mg, 0.0550 mmol) were added to toluene (4 mL) and replaced with argon, and the mixture was stirred at 110° C. for 1 hour using a microwave synthesizer (Monowave 300 manufactured by Anton Paar Gmbh). The reaction solution was returned to room temperature, water was added, and the mixture was extracted with $CH_2Cl_2$. The organic layer was dried over anhydrous $Na_2SO_4$, and the solvent was removed under reduced pressure. A residue was purified by HPLC (eluent, A/B=70/30→0/100, 40 minutes; A: $H_2O$ containing 0.1% TFA (v/v), B: $MeCN/H_2O$=80/20 containing 0.1% TFA (v/v)) to obtain Compound 24 (9.4 mg, 0.017 mmol, yield 7%).

$^1$H-NMR (400 MHz, $CD_3OD$) δ 8.33 (d, J=7.8 Hz, 1H), 7.77-7.86 (m, 2H), 7.39 (d, J=7.8 Hz, 1H), 7.17 (d, J=9.6 Hz, 1H), 7.15 (s, 1H), 7.11 (dd, J=9.6, 2.3 Hz, 1H), 7.00 (d, J=2.3 Hz, 1H), 6.96 (s, 1H), 3.43 (t, J=7.5 Hz, 2H), 3.31 (s, 6H), 3.16 (s, 3H), 2.31 (s, 3H), 1.69-1.78 (m, 2H), 0.93 (t, J=7.3 Hz, 3H); HRMS (ESI$^+$): Calcd for [M]$^+$, 429.2178; found, 429.2194 (+1.6 mmu).

The HPLC chromatogram after purification is shown below. (A/B=80/20→0/100, 25 min; A: $H_2O$ containing 0.1% TFA (v/v), B: $MeCN/H_2O$=80/20 containing 0.1% TFA (v/v). 1.0 mL/min flow rate. Detection at 560 nm).

Synthesis Example 111

Synthesis of Compound 25

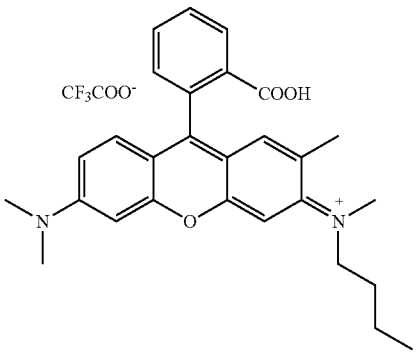

Compound 25

Compound 21 (109 mg, 0.250 mmol), N-methylbutylamine (588 µL, 5.00 mmol), $Cs_2CO_3$ (423 mg, 1.30 mmol), $Pd_2(dba)_3$ (14.6 mg, 0.0159 mmol) and xantphos (26.5 mg, 0.0458 mmol) were added to toluene (10 mL) and replaced with argon, and the mixture was stirred at 100° C. for 22 hours. The reaction solution was returned to room temperature, water was added, and the mixture was extracted with $CH_2Cl_2$. The organic layer was dried over anhydrous $Na_2SO_4$, and the solvent was removed under reduced pressure. A residue was purified by HPLC (eluent, A/B=70/30→0/100; A: $H_2O$ containing 0.1% TFA (v/v), B: $MeCN/H_2O$=80/20 containing 0.1% TFA (v/v)) to obtain Compound 25 (9.3 mg, 0.017 mmol, yield 7%).

$^1$H-NMR (400 MHz, $CD_3OD$) δ 8.34-8.37 (m, 1H), 7.81-7.87 (m, 2H), 7.40-7.43 (m, 1H), 7.20 (d, J=9.2 Hz, 1H), 7.17 (s, 1H), 7.13 (dd, J=10.0, 2.4 Hz, 1H), 7.03 (d, J=2.4 Hz, 1H), 6.99 (s, 1H), 3.49 (t, J=7.6 Hz, 2H), 3.34 (s, 6H), 3.18 (s, 3H), 2.33 (s, 3H), 1.68-1.76 (m, 2H), 1.33-1.42 (m, 2H), 0.96 (t, J=7.2 Hz, 3H); HRMS (ESI$^+$): Calcd for [M]$^+$, 443.2335; found, 443.2364 (+3.0 mDa).

The HPLC chromatogram after purification is shown below. (A/B=80/20→0/100, 25 min; A: H$_2$O containing 0.1% TFA (v/v), B: MeCN/H$_2$O=80/20 containing 0.1% TFA (v/v). 1.0 mL/min flow rate. Detection at 560 nm).

Synthesis Example 12

Synthesis of Compound 26

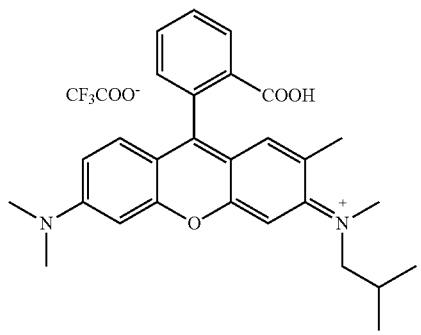

Compound 26

Compound 21 (56.3 mg, 0.129 mmol), N-methylisobutylamine (745 μL, 6.21 mmol), Cs$_2$CO$_3$ (116 mg, 0.356 mmol), and RuPhos Pd G3 (23.6 mg, 0.0282 mmol) were added to toluene (5 mL) and replaced with argon, and the mixture was stirred at 100° C. for 30 minutes using a microwave synthesizer (Monowave 300 manufactured by Anton Paar Gmbh). The reaction solution was returned to room temperature, water was added, and the mixture was extracted with CH$_2$Cl$_2$. The organic layer was dried over anhydrous Na$_2$SO$_4$, and the solvent was removed under reduced pressure. A residue was purified by HPLC (eluent, A/B=70/30→0/100, 40 minutes; A: H$_2$O containing 0.1% TFA (v/v), B: MeCN/H$_2$O=80/20 containing 0.1% TFA (v/v)) to obtain Compound 26 (2.6 mg, 0.0047 mmol, yield 4%).

$^1$H-NMR (400 MHz, CD$_3$OD) δ 8.33 (dd, J=7.8, 1.4 Hz, 1H), 7.82 (dtd, J=20.1, 7.5, 1.5 Hz, 2H), 7.39 (dd, J=7.3, 1.4 Hz, 1H), 7.16-7.19 (m, 2H), 7.11 (dd, J=9.6, 2.3 Hz, 1H), 7.01 (d, J=2.3 Hz, 1H), 6.97 (s, 1H), 3.34 (d, J=7.3 Hz, 2H), 3.32 is, 6H), 3.17 (s, 3H), 2.30 (s, 3H), 2.03-2.13 (m, 1H), 0.90 (dd, J=6.6, 1.6 Hz, 6H); HRMS (ESI$^+$): Calcd for [M]$^+$, 443.2335; found, 443.2354 (+1.9 mmu).

The HPLC chromatogram after purification is shown below. (A/B=80/20→0/100, 25 min; A: H$_2$O containing 0.1% TFA (v/v), B: MeCN/H$_2$O=80/20 containing 0.1% TFA (v/v). 1.0 mL/min flow rate. Detection at 560 nm).

Synthesis Example 131

Synthesis of Compound 27

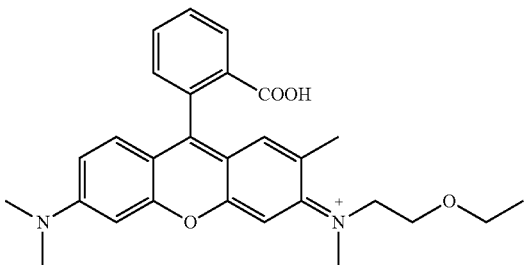

Compound 27

Compound 22 (14.5 mg, 0.267 mmol) and sodium hydride (oiliness, content 50 to 72%) (4.3 mg) were added to DMF (800 μL) and replaced with argon, and the mixture was stirred at 0° C. for 30 minutes. Iodoethane (10.9 μL, 0.136 mmol) was added to the reaction solution, and the mixture was further stirred for 16.5 hours at room temperature. Water was added to the reaction solution, and the mixture was extracted with CH$_2$Cl$_2$. The organic layer was dried over anhydrous Na$_2$SO$_4$, and the solvent was removed under reduced pressure. A residue was purified with reverse phase medium pressure fractionation (eluent, A/B=80/20→10/90; A: H$_2$O containing triethylamine acetate (100 mM), B: MeCN containing triethylamine acetate (100 mM), and A/B=80/20→10/90; A: H$_2$O containing 0.1% TFA (v/v), B: MeCN containing 0.1% TFA (v/v)) to obtain Compound 27 (5.8 mg, 0.010 mmol, yield 38%).

$^1$H-NMR (400 MHz, CD$_3$OD) δ 8.34 (dd, J=7.3 Hz, 1.4 Hz, 1H), 7.77-7.87 (m, 2H), 7.39 (dd, J=7.3 Hz, 1.4 Hz, 1H), 7.23 (s, 1H), 7.18 (d, J=9.6 Hz, 1H), 7.12 (dd, J=9.6 Hz, 2.3 Hz, 1H), 7.02 (d, J=2.3 Hz, 1H), 6.95 (s, 1H), 3.69 (s, 4H), 3.44 (q, J=7.0 Hz, 2H), 3.32 (s, 6H), 3.21 (s, 3H), 2.31 (s, 3H), 1.07 (t, J=6.9 Hz, 3H); HRMS (ESI$^+$): Calcd for [M]$^+$, 459.2284; found, 459.2234 (−5.0 mmu).

The HPLC chromatogram after purification is shown below. (A/B=80/20→0/100, 25 min; A: H$_2$O containing 0.1% TFA (v/v), B: MeCN/H$_2$O=80/20 containing 0.1% TFA (v/v). 1.0 mL/min flow rate. Detection at 560 nm).

Synthesis Example 14

Synthesis of Compound 28

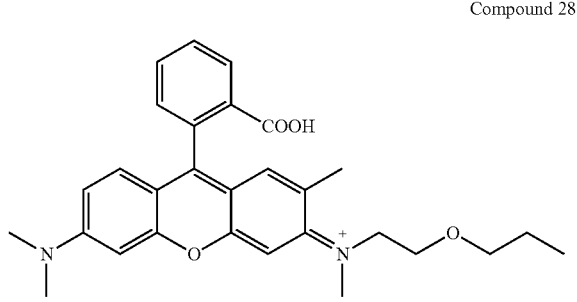

Compound 28

Compound 22 (35 mg, 0.0652 mmol) and sodium hydride (oiliness, content 50 to 72%) (15.7 mg) were added to DMF (1 mL) and replaced with argon, and the mixture was stirred at 0° C. for 30 minutes. Iodopropane (32 μL, 0.329 mmol) was added to the reaction solution, and the mixture was further stirred for 14.5 hours at room temperature. Water was added to the reaction solution, and the mixture was extracted with CH$_2$Cl$_2$. The organic layer was dried over anhydrous Na$_2$SO$_4$, and the solvent was removed under reduced pressure. A residue was purified with reverse phase medium pressure fractionation (eluent, A/B=90/10→10/90; A: H$_2$O containing triethylamine acetate (100 mM), B: MeCN containing triethylamine acetate (100 mM)) and HPLC (eluent, A/B=70/30→0/100; A: H$_2$O containing 0.1% TFA (v/v), B: MeCN containing 0.1% TFA (v/v)) to obtain Compound 28 (13.0 mg, 0.0222 mmol, yield 34%).

$^1$H-NMR (400 MHz, CD$_3$OD) δ 8.33 (dd, J=7.8, 1.4 Hz, 1H), 7.77-7.86 (m, 2H), 7.38 (dd, J=7.5 Hz, 1.1 Hz, 1H), 7.22 (s, 1H), 7.18 (d, J=9.6 Hz, 1H), 7.11 (dd, J=9.6 Hz, 2.3 Hz, 1H), 7.01 (d, J=2.3 Hz, 1H), 6.95 (s, 1H), 3.66-3.72 (m, 4H), 3.32-3.35 (m, 8H), 3.21 (s, 3H), 2.31 (s, 3H), 1.42-1.51 (m,

2H), 0.81 (t, J=7.6 Hz, 3H); $^{13}$C-NMR (100 MHz, CD$_3$OD) δ 168.0, 162.9, 161.4, 159.5, 159.5, 157.1, 135.4, 133.9, 133.0, 132.5, 132.3, 132.3, 131.6, 131.4, 130.3, 116.6, 116.2, 104.2, 97.3, 73.9, 69.3, 55.5, 41.7, 41.1, 23.9, 21.8, 10.9; HRMS (ESI$^+$): Calcd for [M]$^+$, 473.2440; found, 473.2407 (−3.3 mmu).

Synthesis Example 15

Synthesis of Compound 29

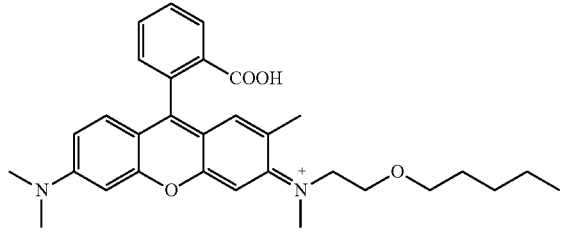

Compound 29

Compound 22 (89.7 mg, 0.165 mmol) and sodium hydride (oiliness, content 50 to 72%) (46.3 mg) were added to DMF (1 mL) and replaced with argon, and the mixture was stirred at 0° C. for 30 minutes. Iodopentane (135 µL, 1.04 mmol) was added to the reaction solution, and the mixture was further stirred for 17 hours at room temperature. The mixture was neutralized with 2N hydrochloric acid, saturated aqueous ammonium chloride solution was added, and the mixture was extracted with ethyl acetate. The organic layer was dried over anhydrous Na$_2$SO$_4$, and the solvent was removed under reduced pressure. A residue was purified with reverse phase medium pressure fractionation (eluent, A/B=90/10→0/100; A: H$_2$O containing 0.1% TFA (v/v), B: MeCN containing 0.1% TFA (v/v)) to obtain Compound 29 (58.3 mg, 0.0949 mmol, yield 58%).

$^1$H-NMR (400 MHz, CD$_3$OD) δ 8.36 (dd, J=7.5, 1.1 Hz, 1H), 7.79-7.89 (m, 2H), 7.40 (dd, J=7.3, 0.9 Hz, 1H), 7.23 (s, 1H), 7.20 (d, J=9.6 Hz, 1H), 7.13 (dd, J=9.6, 2.3 Hz, 1H), 7.00 (d, J=2.3 Hz, 1H), 6.98 (s, 1H), 3.67-3.78 (m, 4H), 3.39 (t, J=6.4 Hz, 2H), 3.32 (s, 6H), 3.23 (s, 3H), 2.33 (s, 3H), 1.43-1.50 (m, 2H), 1.22-1.27 (m, 4H), 0.82 (t, J=7.1 Hz, 3H); $^{13}$C-NMR (101 MHz, CD$_3$OD) δ 167.5, 162.5, 161.3, 159.0, 159.0, 156.7, 134.8, 133.5, 132.6, 132.2, 131.9, 131.8, 131.2, 131.0, 129.8, 116.2, 116.1, 115.8, 103.7, 96.9, 71.8, 68.9, 55.1, 41.2, 40.7, 30.1, 29.1, 23.1, 21.5, 14.0; HRMS (ESI$^+$): Calcd for [M]$^+$, 501.2753; found, 501.2734 (−1.9 mDa).

Example 7

Development of Novel Fluorescent Probe Capable of Detecting N-Dealkylation Activity of P450 (2)

Regarding the compounds synthesized in Synthesis Examples 8 to 15, it was examined under the same conditions as in Example 6 whether the increase in fluorescence was observed when each compound was metabolized by P450. The results are illustrated in FIG. 14 and FIG. 15.

FIG. 14 illustrates time-dependent fluorescence changes of a NADPH producing system (MgCl$_2$: 1.5 mM, glucose-6-phosphate: 3 mM, NADP$^+$: 0.3 mM, glucose-6-phosphate dehydrogenase: 0.5 U/mL) and 1 µM rhodamine derivatives (Compounds 23 to 26) using 11 types of P450 subtypes in 0.1M potassium phosphate buffer (pH 7.4) (excitation wavelength: 544 nm/detection wavelength: 590 nm).

As illustrated in FIG. 14, similar to the results of Example 6, these compounds are metabolized by CYP3A, but are also metabolized by other P450 molecular species.

FIG. 15 illustrates time-dependent fluorescence changes of a NADPH producing system (MgCl$_2$: 1.5 mM, glucose-6-phosphate: 3 mM, NADP$^+$: 0.3 mM, glucose-6-phosphate dehydrogenase: 0.5 U/mL) and 1 µM rhodamine derivatives (Compounds 22 and 27 to 29) using 11 types of P450 subtypes in 0.1M potassium phosphate buffer (pH 7.4) (excitation wavelength: 544 nm/detection wavelength: 590 nm).

As illustrated in FIG. 15, it has been found that several non-fluorescent rhodamines are selectively metabolized by CYP3A among the major P450 molecular species.

Example 8

Next, as a representative of the compounds illustrated in FIG. 15, absorption/fluorescence spectrum changes when Compound 29 (illustrated below) was reacted with CYP3A4 were shown (FIG. 16). Shortening the absorption wavelength due to N-dealkylation of rhodamine (a) and a significant increase in fluorescence intensity (b and c) were observed.

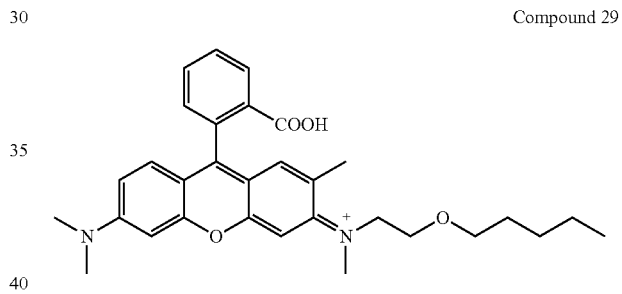

Compound 29

Here, FIG. 16 illustrates changes in absorption over time (a) and fluorescence (b and c) of 1 µM compound 29 in 0.1M potassium phosphate buffer (pH 7.4) using a CYP3A4 (10 nM) and NADPH producing system (MgCl$_2$: 1.5 mM, glucose-6-phosphate: 3 mM, NADP$^+$: 0.3 mM, glucose-6-phosphate dehydrogenase: 0.5 U/mL) (excitation wavelength: 520 nm).

Compound 29 also showed the increase in fluorescence due to the reaction with human liver microsomes (XENO-TECH: XTreme 200 Human Liver Microsomes), and the increase was suppressed by addition of ketoconazole, which was an inhibitor that strongly inhibited CYP3A (FIG. 17). Therefore, it became clear that Compound 29 could detect the activity of CYP3A by fluorescence even in human liver microsomes.

Here, FIG. 17 illustrates time-dependent fluorescence change of Compound 29 (1 µM) in in 0.1M potassium phosphate buffer (pH 7.4) using an NADPH producing system (MgCl$_2$: 1.5 mM, glucose-6-phosphate: 3 mM, NADP$^+$: 0.3 mM, glucose-6-phosphate dehydrogenase: 0.5 U/mL) and human liver microsomes (0.05 mg/mL) (Ex.544 nm/Em.590 nm). The human liver microsomes and the NADPH producing system were pre-incubated with 0.1% DMSO or 10 µM ketoconazole for 30 minutes before addition of Compound 29, and the measurement was started immediately after addition of Compound 29.

Example 9

Next, it was examined whether Compound 29 could detect the CYP3A activity in living cells.

HepaRG (registered trademark) frozen vial 8M (HPR116-8M) purchased from KAC Co., Ltd. was thawed and inoculated according to the manufacturer's protocol, and cultured for 6 days in an 8-well chamber (Matsunami: SCC-038 collagen coat). Then, it was examined whether Compound 29 could detect the CYP3A activity of HepaRG.

Imaging was performed on three types of control group, inhibitor-added group, and derivative-added group.

Ketoconazole was used as an inhibitor. Rifampicin was used as an inducer of the CYP3A activity. For 3 days immediately before imaging, 20 µM of rifampicin was added to the derivative-added group, and 0.1% DMSO was added as a vehicle to the control group and the inhibitor-added group.

Imaging was performed according to the following protocol.

Protocol
Remove culture medium
Wash with PBS (pH 7.4) three times
Add 200 µL DMEM (not containing phenol red) (containing 10 µM of ketoconazole (inhibitor-added group) or 0.1% DMSO (control, inducer-added group))
Incubate at 37° C. for 30 minutes
Add 0.2 µL of Compound 29 (final concentration 1 µM)
Incubate at 37° C. for 30 minutes
Imaging by Leica TSC SP8

FIG. 18 illustrates an imaging image.

FIG. 19 illustrates a graph showing a distribution of the fluorescence intensity when a total of 20 cells (2 wells×2 fields×5 cells) from each group are enclosed by ROI.

Here, FIG. 18 illustrates a fluorescence image (control) of HepaRG obtained when HepaRG to which 0.1% DMSO was added for 3 days was pretreated with 0.1% DMSO for 30 minutes, then 1 µM of Compound 29 was added, and the mixture was incubated at 37° C. for 30 minutes, a fluorescence image (+ inhibitor) of HepaRG obtained when 0.1% DMSO was added for 3 days and pretreated with 1 µM ketoconazole for 30 minutes before imaging, then Compound 29 was added, and the mixture was incubated at 37° C. for 30 minutes, and a fluorescence image obtained when 20 µM rifampicin were added for 3 days and was pretreated with 0.1% DMSO for 30 minutes, then Compound 29 was added, and the mixture was further incubated at 37° C. for 30 minutes.

The image was taken (40 magnifications) using a confocal microscope equipped with an Ar laser and an objective lens. Conditions: Excitation wavelength 514 nm, detection wavelength 540 to 590 nm (PMT1).

FIG. 19 shows a box plot illustrating a distribution of fluorescence intensity of 20 cells selected from each group in the experiment of FIG. 18.

Since strong fluorescence was observed in the control group and the derivative-added group as compared with the inhibitor-added group, it became clear that Compound 29 could detect the CYP3A activity even in living cells.

Although human primary frozen hepatocytes are currently used for drug metabolism tests in the drug discovery process, the cells have problems such as differences among donors and difficulty in stable supply On the other hand, human iPS cell-derived hepatocytes are considered to be alternative cells of human primary frozen hepatocytes, and studies to differentiate and induce human iPS cells into hepatocytes are currently being actively conducted. In the study of differentiation and induction into hepatocytes, the activity of CYP3A4 may be used as an index for maturation from iPS cells to hepatocytes in some cases. Development of a CYP3A activity selective fluorescent probe that can be used in living cells is considered to become a tool that visualizes the maturation of iPS cell-derived hepatocytes, and it is expected that the CYP3A activity selective fluorescent probe contributes to development of more practical iPS cell-derived hepatocytes.

What is claimed is:

1. A compound represented by the following general formula (I) or a salt thereof:

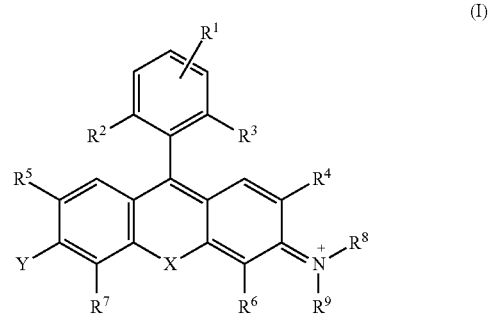

where:

$R^1$ represents a hydrogen atom or one to three monovalent substituent groups present on a benzene ring, which are the same or different;

said monovalent substituent group is selected from the group consisting of an alkyl group having 1 to 14, an alkenyl group having 1 to 6 carbon atoms, an alkynyl group having 1 to 6 carbon atoms, an alkoxy group having 1 to 14 carbon atoms, a hydroxyl group, a carboxy group, a sulfonyl group, an alkoxycarbonyl group, a halogen atom, an amino group, an amide group and an alkylamido group, and said monovalent substituent groups may furthermore have any of one or more substituent groups;

$R^2$ and $R^3$ are, each independently, a hydrogen atom or a monovalent substituent group present on a benzene ring, said monovalent substituent group is selected from an alkyl group having 1 to 6 carbon atoms, an alkoxy group having 1 to 6 carbon atoms, a carboxyl group and an ester group;

$R^4$ and $R^5$ are, each independently, a hydrogen atom, a substituted or unsubstituted alkyl group having 1 to 6 carbon atoms, a carboxyl group, an ester group, an amide group, or a halogen atom;

$R^6$ and $R^7$ are, each independently, a hydrogen atom, a substituted or unsubstituted alkyl group having 1 to 6 carbon atoms, a carboxyl group, an ester group, an amide group, or a halogen atom;

provided that any one or more of $R^4$, $R^5$, $R^6$, and $R^7$ are substituents other than a hydrogen atom;

$R^8$ and $R^9$ are, each independently, a hydrogen atom or a substituted or unsubstituted alkyl group having 1 to 14 carbon atoms, or $R^8$ and $R^9$ together optionally form a 4-7 membered heterocyclyl containing a nitrogen atom to which $R^8$ and $R^9$ are bonded;

X is selected from an oxygen atom, $Si(R^a)(R^b)$, $C(R^a)(R^b)$, $Ge(R^a)(R^b)$, $P(=O)R^c$, $SO_2$ and Se where:
R$^a$ and R$^b$ are, each independently, an alkyl group having 1 to 6 carbon atoms or an aryl group optionally being substituted, and R$^c$ is an alkyl group having 1 to 6 carbon atoms or a phenyl group optionally being substituted;

Y is —NR$^{10}$R$^{11}$ or —OH, where:
R$^{10}$ and R$^{11}$ are, each independently, a hydrogen atom or a substituted or unsubstituted alkyl group having 1 to 14 carbon atoms, or R$^{10}$ and R$^{11}$ together optionally form a 4-7 membered heterocyclyl containing a nitrogen atom to which R$^{10}$ and R$^{11}$ are bonded;

wherein:
(i) when Y is —NR$^{10}$R$^{11}$,
where:
(1) R$^8$, R$^9$, R$^{10}$ and R$^{11}$ are substituted or unsubstituted alkyl groups having 1 to 6 carbon atoms, which are the same or different, any one or more of R$^4$ and R$^6$ and/or any one or more of R$^5$ and R$^7$ are substituents other than a hydrogen atom, and at least one of the alkyl groups of R$^8$, R$^9$, R$^{10}$ and R$^{11}$ is an alkyl group substituted with a hydroxyl or an alkoxy group group, wherein at least one of substituents at the ortho position with respect to the amino group on the xanthene ring to which the alkyl group substituted with a hydroxyl group or an alkoxy group group is bonded is a substituent other than a hydrogen atom, or (2) in any one of the pair of R$^8$ and R$^9$ and the pair of R$^{10}$ and R$^{11}$, all groups are substituted or unsubstituted alkyl groups having 1 to 6 carbon atoms, which are the same or different, and at least one of the alkyl groups is an alkyl group substituted with a hydroxyl group or an alkoxy group, where,
when R$^8$ and R$^9$ are both the same or different substituted or unsubstituted alkyl groups having 1 to 6 carbon atoms, any one or more of R$^4$ and R$^6$ are substituents other than a hydrogen atom, or when R$^{10}$ and R$^{11}$ are both the same or different substituted or unsubstituted alkyl groups having 1 to 6 carbon atoms, any one or more of R$^5$ and R$^7$ are substituents other than a hydrogen atom;

and (ii) when Y is —OH,
R$^8$ and R$^9$ are both substituents other than a hydrogen atom, and any one or more of R$^4$ and R$^6$ are substituted or unsubstituted alkyl groups having 1 to 6 carbon atoms or a halogen atom.

2. The compound or salt thereof according to claim 1, wherein Y is —NR$^{10}$R$^{11}$.

3. A fluorescent probe for detecting P450 activity comprising the compound or salt thereof according to claim 1.

4. A method of detecting P450 in a cell comprising:
(a) introducing the fluorescent probe according to claim 3 into the cell; and,
(b) measuring fluorescence emitted in the cell by the fluorescent probe.

5. A compound represented by any one of the following formulae

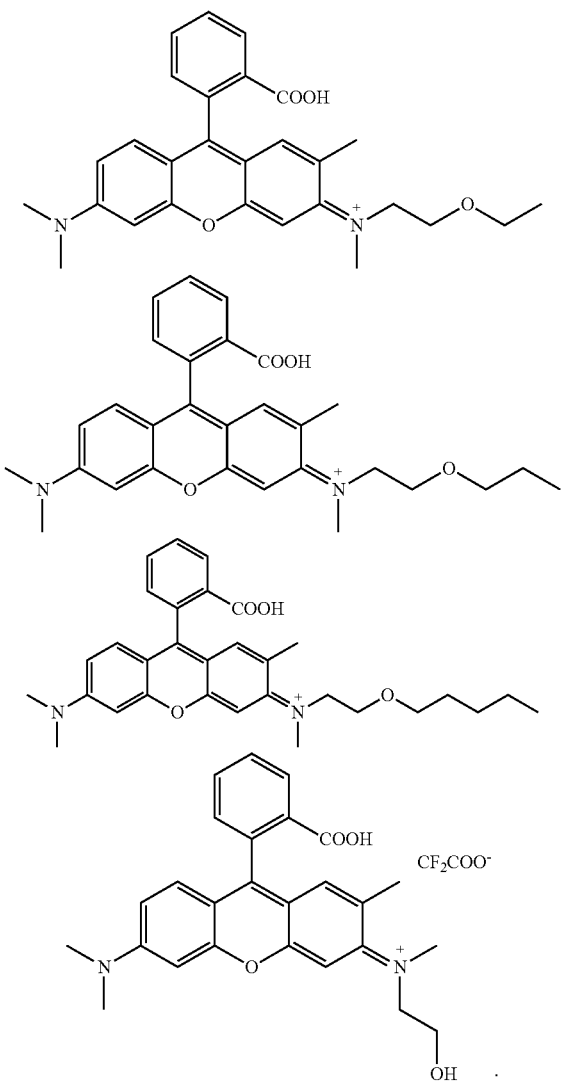

* * * * *